United States Patent
Boyle, Jr.

(10) Patent No.: US 11,331,087 B2
(45) Date of Patent: May 17, 2022

(54) MINIMALLY INVASIVE METHODS AND APPARATUS

(71) Applicant: Edward M. Boyle, Jr., Bend, OR (US)

(72) Inventor: Edward M. Boyle, Jr., Bend, OR (US)

(73) Assignee: PRECISION THORACIC, LLC, Irvine, CA (US)

(*) Notice: Subject to any disclaimer, the term of this patent is extended or adjusted under 35 U.S.C. 154(b) by 1168 days.

(21) Appl. No.: 15/340,170

(22) Filed: Nov. 1, 2016

(65) Prior Publication Data

US 2017/0042516 A1 Feb. 16, 2017

Related U.S. Application Data

(63) Continuation of application No. 14/271,186, filed on May 6, 2014, now abandoned, which is a continuation
(Continued)

(51) Int. Cl.
*A61B 10/02* (2006.01)
*A61B 17/00* (2006.01)
(Continued)

(52) U.S. Cl.
CPC .......... *A61B 10/0266* (2013.01); *A61B 10/04* (2013.01); *A61B 17/0057* (2013.01);
(Continued)

(58) Field of Classification Search
CPC ............ A61B 10/0266; A61B 17/0057; A61B 17/12159; A61B 17/320016;
(Continued)

(56) References Cited

U.S. PATENT DOCUMENTS 4,007,732 A 2/1977 Kvavle et al.
5,190,561 A 3/1993 Graber
(Continued)

FOREIGN PATENT DOCUMENTS

WO 9603163 A1 2/1996
WO 2005/110508 A2 11/2005

OTHER PUBLICATIONS

International Search Report in related patent application No. PCT/US06/29347 dated Aug. 4, 2008, 2 pages.

*Primary Examiner* — Devin B Henson
(74) *Attorney, Agent, or Firm* — Pearne & Gordon LLP

(57) ABSTRACT

Methods and apparatus are provided to facilitate the minimally invasive removal of tissue biopsies and to facilitate the direct approach to anesthetizing the chest wall, in accordance with embodiments of the present invention. A pull-type cutting device 1 comprises two coaxially nested tubes, each extending from a proximal end 21 to a distal end 22. The first tube 61 defines a guide wire lumen 23 for slidingly receiving a guide wire. The second tube 63 extends over the first tube 60 and coupled thereto at the distal end 22 defining an expandable portion 13 adjacent the distal end 22. The second tube 63 defines an inflation lumen 25 extending from the shaft proximal end 21 to the expandable portion 13. The inflation lumen 25 communicates inflation fluid from the proximal end 21 to the expandable portion 13 so as to inflate and deploy the expandable portion 13. Disposed adjacent the shaft distal end 22 is a cutting head 10 comprising the expandable portion 13 having a cutting portion 11 distal from the shaft distal end 22.

16 Claims, 27 Drawing Sheets

Related U.S. Application Data of application No. 11/996,944, filed as application No. PCT/US2006/029347 on Jul. 26, 2006, now Pat. No. 8,734,362.

(60) Provisional application No. 60/702,801, filed on Jul. 26, 2005.

(51) Int. Cl.

| | | |
|---|---|---|
| *A61B 17/12* | (2006.01) | |
| *A61B 17/32* | (2006.01) | |
| *A61B 17/3205* | (2006.01) | |
| *A61B 17/3207* | (2006.01) | |
| *A61B 18/14* | (2006.01) | |
| *A61B 18/20* | (2006.01) | |
| *A61M 25/10* | (2013.01) | |
| *A61B 10/04* | (2006.01) | |
| *A61B 34/20* | (2016.01) | |
| *A61B 18/04* | (2006.01) | |
| *A61B 17/22* | (2006.01) | |
| *A61M 25/00* | (2006.01) | |
| *A61B 17/30* | (2006.01) | |
| *A61B 10/00* | (2006.01) | |
| *A61B 18/00* | (2006.01) | |
| *A61B 17/221* | (2006.01) | |
| *A61B 17/3209* | (2006.01) | |
| *A61M 25/09* | (2006.01) | |

(52) U.S. Cl.
CPC .... *A61B 17/1204* (2013.01); *A61B 17/12022* (2013.01); *A61B 17/12104* (2013.01); *A61B 17/12159* (2013.01); *A61B 17/320016* (2013.01); *A61B 17/32053* (2013.01); *A61B 17/32056* (2013.01); *A61B 17/320725* (2013.01); *A61B 18/04* (2013.01); *A61B 18/14* (2013.01); *A61B 18/20* (2013.01); *A61B 34/20* (2016.02); *A61M 25/10* (2013.01); *A61B 10/0283* (2013.01); *A61B 17/221* (2013.01); *A61B 17/32075* (2013.01); *A61B 17/32093* (2013.01); *A61B 2010/0006* (2013.01); *A61B 2017/00247* (2013.01); *A61B 2017/00296* (2013.01); *A61B 2017/00535* (2013.01); *A61B 2017/00575* (2013.01); *A61B 2017/00592* (2013.01); *A61B 2017/00606* (2013.01); *A61B 2017/00809* (2013.01); *A61B 2017/22034* (2013.01); *A61B 2017/22038* (2013.01); *A61B 2017/22061* (2013.01); *A61B 2017/306* (2013.01); *A61B 2018/00029* (2013.01); *A61B 2018/0063* (2013.01); *A61B 2018/00392* (2013.01); *A61B 2018/00595* (2013.01); *A61M 25/0045* (2013.01); *A61M 25/09* (2013.01); *A61M 2025/105* (2013.01); *A61M 2025/1013* (2013.01); *A61M 2025/1081* (2013.01); *A61M 2025/1086* (2013.01)

(58) Field of Classification Search
CPC ........ A61B 17/32053; A61B 17/32056; A61B 17/320725; A61B 17/221; A61B 17/32075; A61B 2018/141; A61B 2018/00595; A61B 2018/0063

See application file for complete search history.

(56) References Cited

U.S. PATENT DOCUMENTS

| | | | |
|---|---|---|---|
| 5,196,024 A | 3/1993 | Barath | |
| 5,353,804 A | 10/1994 | Kornberg et al. | |
| 5,643,282 A | 7/1997 | Kieturakis | |
| 5,681,281 A | 10/1997 | Vigil et al. | |
| 5,779,698 A | 7/1998 | Clayman et al. | |
| 5,908,435 A | 6/1999 | Samuels | |
| 5,928,163 A * | 7/1999 | Roberts | A61B 18/1445 600/567 |
| 5,961,526 A | 10/1999 | Chu et al. | |
| 6,213,957 B1 | 4/2001 | Milliman et al. | |
| 6,258,108 B1 | 7/2001 | Lary | |
| 6,652,520 B2 | 11/2003 | Moorman et al. | |
| 6,770,070 B1 | 8/2004 | Balbierz | |
| 7,517,352 B2 | 4/2009 | Evans et al. | |
| 7,811,303 B2 | 10/2010 | Fallin et al. | |
| 2002/0019597 A1 | 2/2002 | Dubrul et al. | |
| 2002/0095101 A1 | 7/2002 | Fontenot | |
| 2004/0010206 A1* | 1/2004 | Dubrul | A61B 10/0266 600/567 |
| 2004/0122349 A1* | 6/2004 | Lafontaine | A61B 17/0057 604/11 |
| 2006/0025815 A1 | 2/2006 | McGurk et al. | |
| 2006/0074484 A1 | 4/2006 | Huber | |
| 2006/0190037 A1* | 8/2006 | Ginn | A61B 17/0057 606/213 |
| 2007/0073343 A1 | 3/2007 | Jahns et al. | |
| 2009/0054805 A1 | 2/2009 | Boyle, Jr. | |
| 2009/0105745 A1 | 4/2009 | Culbert | |
| 2012/0316608 A1 | 12/2012 | Foley | |

\* cited by examiner

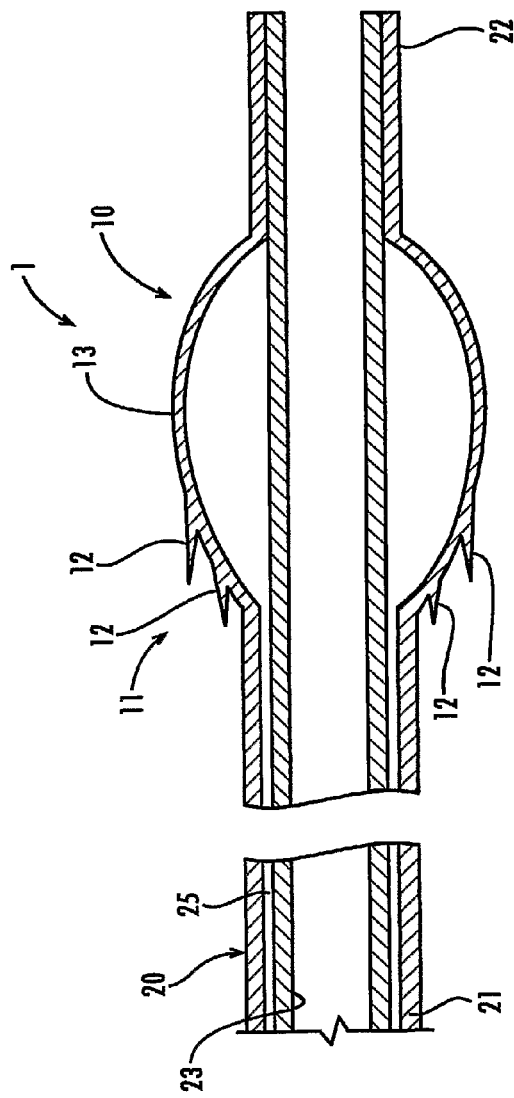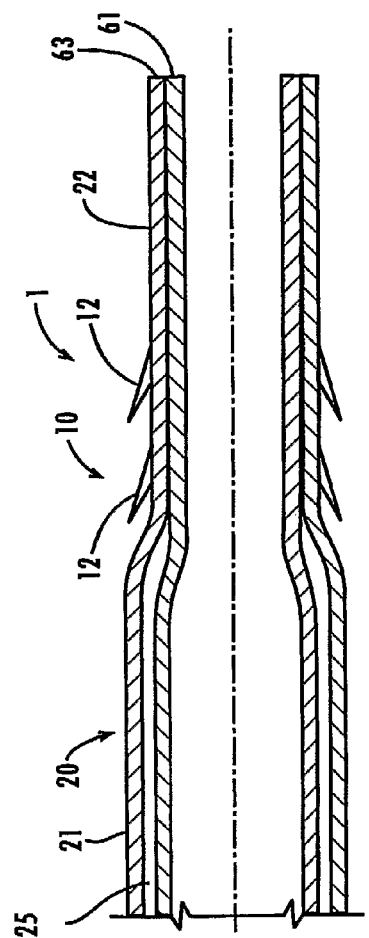

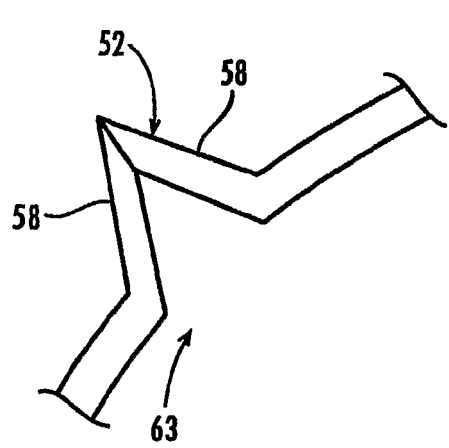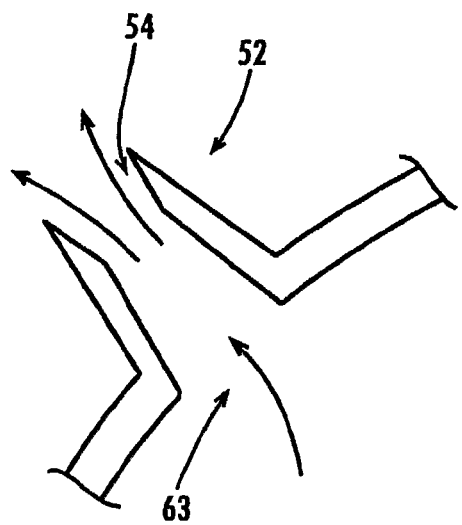
Fig. 9A  Fig. 9B
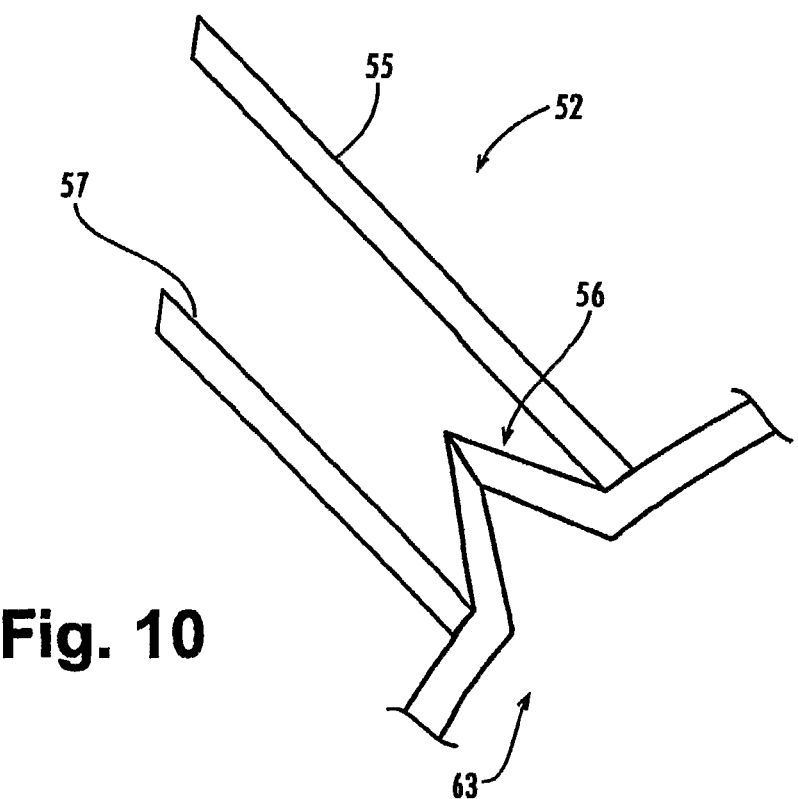
Fig. 10

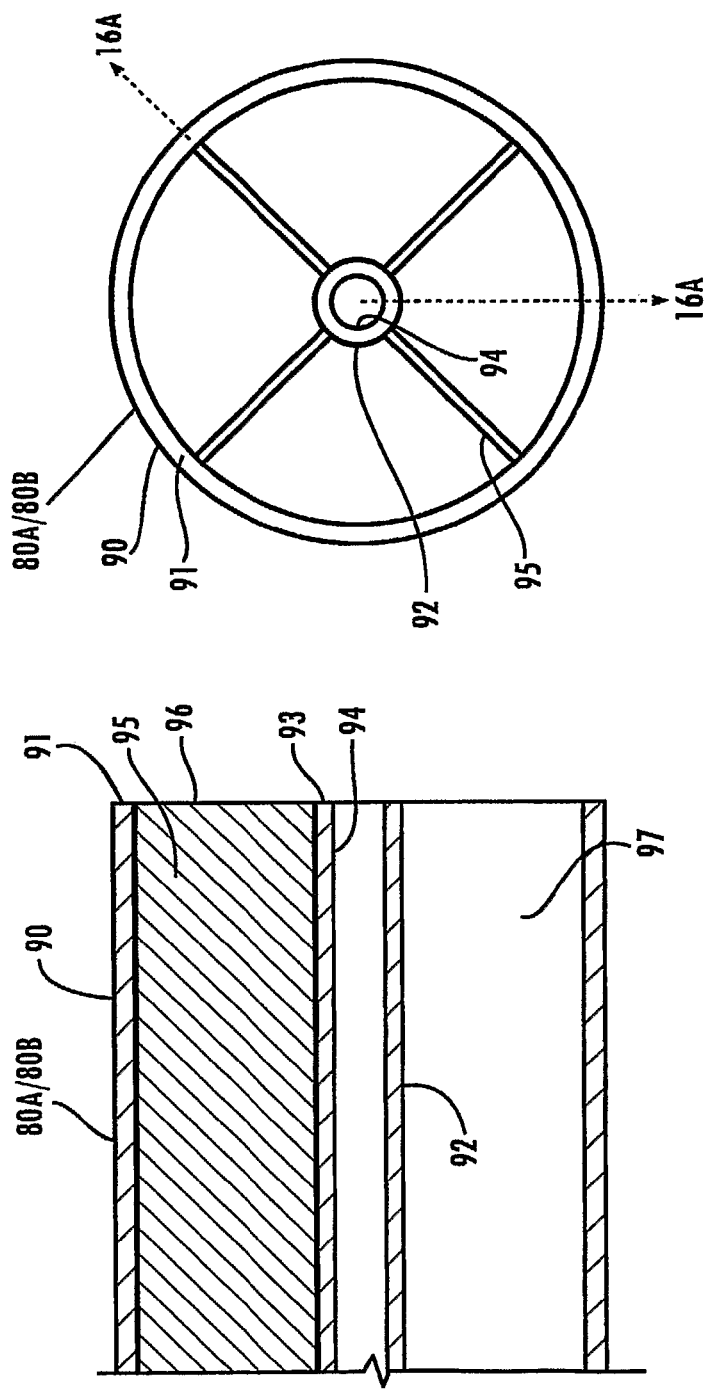

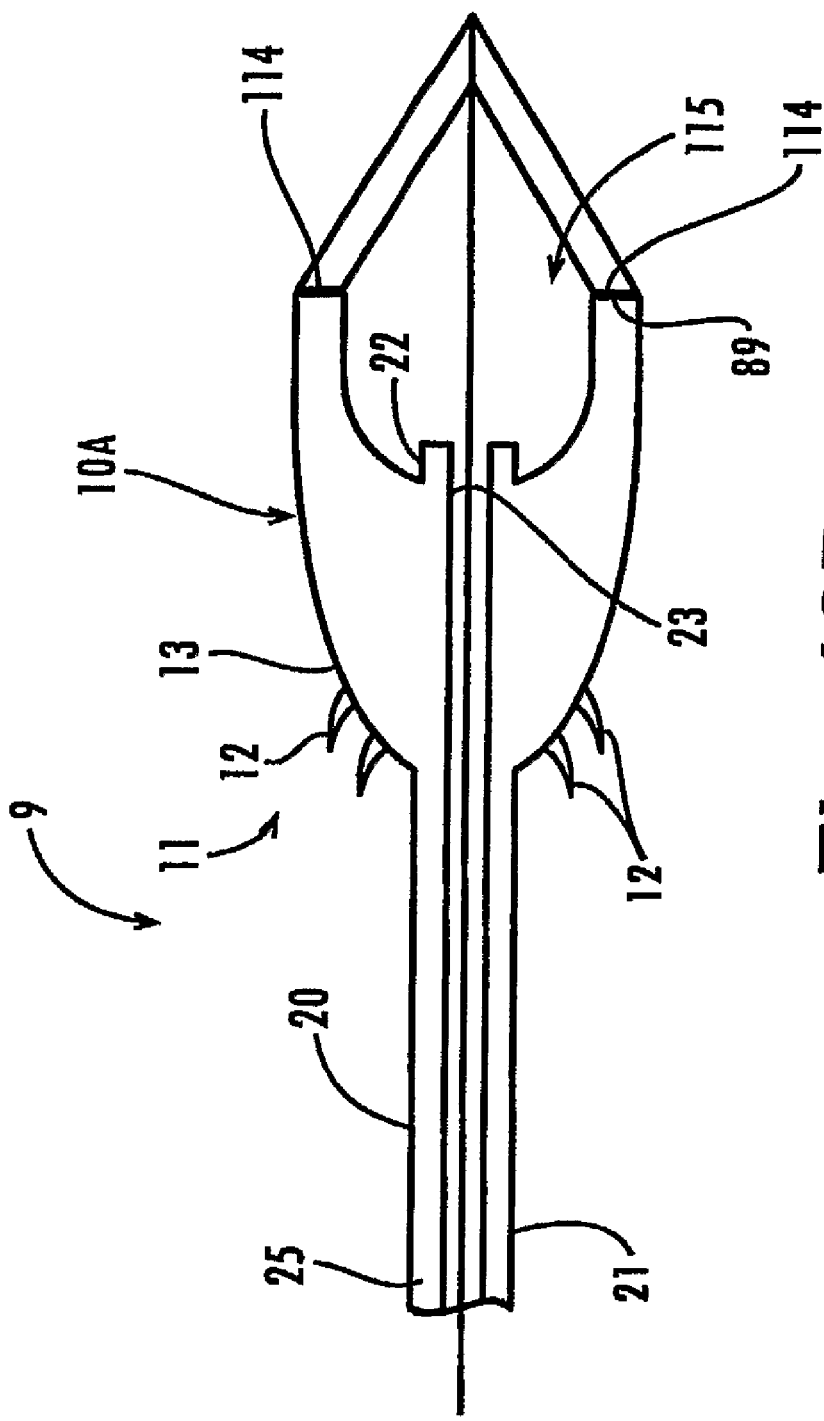

MINIMALLY INVASIVE METHODS AND APPARATUS

RELATED APPLICATION

This application is a continuation of U.S. patent application Ser. No. 14/271,186 filed May 6, 2014, which was a continuation of U.S. patent application Ser. No. 11/996,944 filed Jul. 18, 2008, now U.S. Pat. No. 8,734,362, which was the US national stage under 35 USC §371 of PCT patent application No. PCT/US2006/29347 filed Jul. 26, 2006, which claims the benefit of U.S. Provisional application No. 60/702,801, filed on Jul. 26, 2005, all of which are in their entirety incorporated herein by reference.

FIELD OF THE INVENTION

The present invention is related to surgical tools and methods.

BACKGROUND

According to the American Lung Association, each year over 344,000 Americans die of lung disease, making it the third most frequent cause of death in this country. An even more staggering statistic is that an additional 35 million Americans are living with chronic, debilitating lung diseases. Not uncommonly, patients with lung disease or at risk for lung disease undergo various forms of thoracic imaging. This has led to an unprecedented number of patients presenting to lung specialists with nodular abnormalities suspicious for cancer or interstitial abnormalities suspicious for various forms of Interstitial Lung Disease (ILD). When a patient is found with these abnormalities, it is often necessary to biopsy the tissue to establish the diagnosis, the prognosis, and guide further therapy.

One of the factors that contribute to lung disease is smoking. According to the Center for Disease Control, there are 94 million past and current smokers in the US. Half are over the age of 45 (the age at which lung cancer incidences increase). Many smokers are concerned about the risk of developing lung cancer, which explains the growing success of CT based lung cancer screening programs. The problem with these programs is that about 30% of the screened patients will have suspicious nodules suggestive of cancer, but only a small percentage are ultimately proven to be cancer. While there is considerable evidence to suggest that CT based lung cancer early detection programs are beneficial in detecting early stage lung cancer, the area of biggest clinical unmet need is in the ability to differentiate between a benign and malignant nodule. The currently available lung biopsy techniques, such as CT guided biopsy, bronchoscopy, thoracoscopy or thoracotomy are either too insensitive or too invasive, limiting their usefulness and making the determination difficult at best. Thus one of the most significantly limiting factors that has prevented success of lung cancer screening programs has been a lack of safe and effective ways to sample lung tissue in a minimally invasive fashion.

A similar dilemma exists for the diagnosis of interstitial lung disease. In a number of cases where there is a suspicious imaging pattern suggestive of ILD or cancer, it is desirable to sample the tissue so that a pathologist can establish the exact cause of the abnormality. The problem is that the current lung biopsy techniques are invasive, painful and many require general anesthesia, which is not always well tolerated in patients with impaired lung function. Many patients are judged "not a surgical candidate," due to the patient's degree of medical disability and lung dysfunction. Both thoracotomy (a large incision through the chest muscles and between the ribs) and thoracoscopy (the use of a scope and other working ports through the ribs to operate in the space around the lung) can be very disabling and painful. In fact, these forms of surgery are generally much more painful and disabling than other forms of surgery, such as heart surgery and abdominal surgery due to the manipulation of the chest wall muscles, ribs and intercostal nerves between the ribs. Currently, thoracotomy and thoracoscopy often require long hospital stays and even longer recovery times. Both procedures can lead to chronic pain syndromes in a surprisingly high percentage of patients.

When a determination is made to biopsy a lung nodule 510, there are several options, as illustrated in FIG. 1. One option is to use a bronchoscopic approach. This, however, is most useful for larger, more central tumors. Generally, a central approach is not a useful option for the more common small nodules since most lung nodules 510 are in the periphery 501 of the lung 502 and not connected to the airway 503. Another option is to use a CT guided needle biopsy 522 of the lung 502. While this approach can be useful in larger, more peripheral tumors, it is not particularly helpful for smaller nodules 510 that are deeper in the lung 502. Furthermore, only a small core sampling of the tissue can be taken, and thus false negative biopsies are common. Additionally, since there is no mechanism to seal the lung 502, bleeding complications and pneumothorax are frequent concerns, occurring in nearly 20% of patients.

Thoracic surgical approaches to biopsy lung nodules can be divided into two categories: thoracotomy and thoracoscopy. A thoracotomy 530 is a 300 to 450 mm (12 to 18 inches) incision 532 on the chest wall skin 304, followed by division or dissection of the major back muscles to move them out of the way, partial removal of the rib 42, and the placement of a rib spreader 534 to provide intra thoracic access to the operating surgeon. The advantage of a thoracotomy is that the surgeon has excellent access to the intrathoracic structures, and can see and manually feel the lung 502 and other structures directly. This is especially important when targeting a tiny lung nodule 510. The major disadvantage is the degree of pain and the potential for complications related to the magnitude of the incision. A thoracotomy is well known to be a very painful operation for the patient, with significant acute and chronic pain issues. Because of the degree of invasiveness, it is reserved only for the most optimal surgical candidates as many patients with significant lung disease cannot tolerate a thoracotomy and recover without significant morbidity and mortality. For these reasons it is recognized that there is a need in the art to lessen the invasiveness of thoracic surgery.

One approach that has been around for many years is to utilize an endoscope 542 to facilitate visualization within in the chest, thereby precluding the need for a large thoracotomy incision. Thoracoscopy 540 is the use of a specialized viewing instrument, usually a rigid endoscope 542, introduced through a thoracostomy, or a small hole placed in between the ribs 42. Once the endoscope 542 is placed in the space that surrounds the lung 502, known as the pleural space, usually two to three additional thoracostomy holes are made to introduce additional instruments 544. Additional instruments 544 include grasping instruments, cutting instruments, and in the case of a thoracoscopic lung biopsy, a cutting stapler, such as the Ethicon Endosurgery Endo GIA 45 mm stapler. Using the endoscope 542 and the other instruments 544, a "triangulation" technique is utilized where, for example, the endoscope 542 is used to view as the grasping instrument is brought in from one direction, and the stapler is brought in from another, and tissue is cut with the stapler and removed through one of the ports.

One of the major disadvantages of this approach is the number and size of ports needed to triangulate in order to carry out the biopsy. While this approach is commonplace in most laparoscopic operations carried out in the abdomen, such as the laparoscopic cholecycstecomy, there are unique features of an endothoracic operation that make this approach undesirable. First, it is almost always necessary to utilize a general anesthetic to perform a thoracoscopic lung biopsy. In addition, it is nearly always necessary to utilize a specially placed, and more complicated dual lumen endrotracheal tube so that artificial ventilation can be delivered to the opposite lung, and excluded to the side of the lung that is being biopsied. This technique, known as single lung ventilation, is needed for nearly all current thoracoscopic operations. Many patients with end stage lung disease, however, are unable to tolerate a general anesthetic, and of those that tolerate a general anesthetic, many cannot tolerate single lung ventilation because their respiratory reserve is so limited. Additionally, the intercostal spaces are particularly sensitive to pressure, as there is a fixed and limited space between the ribs, and the intercostal nerve runs underneath each rib in the intercostal space. Each time a thoracostomy is performed, pain can be severe and prolonged. This is especially the case with larger thoracostomy port sizes, such as 10 mm and 12 mm ports that are commonly used for contemporary thoracoscopy. Some studies have estimated that as many as one third of patients have chronic pain in their chest wall up to one year after thoracoscopy, and it is believed this is due to intercostal nerve irritation that occurs when multiple, large ports are introduced into the pleural space between the ribs. Single port procedures have been reported in the literature for very limited procedures, but they generally require very large incisions, 30 mm or more, to get multiple instruments through a single port.

Because of the drawbacks of bronchoscopy, open lung biopsy, and thoracoscopy, a large percentage of patients are simply not referred for lung biopsy because the referring physician is uncomfortable with the degree of invasiveness coupled with the accuracy of the available techniques. Given the advancements in imaging and the improved appreciation of the value of tissue diagnosis in lung disease, new techniques are needed to biopsy the lung in a precise, minimally invasive manner.

BRIEF DESCRIPTION OF THE DRAWINGS

Like reference numbers generally indicate corresponding elements in the figures.

FIGS. 2A and 2B are side cross-sectional views of a pull-type cutting device in an expanded and deflated configuration, respectively, in accordance with an embodiment of the present invention;

FIGS. 9A and 9B are side cross-sectional views of a delivery element, in accordance with embodiments of the present invention;

FIG. 10 is a side cross-sectional view of a delivery element, in accordance with an embodiment of the present invention;

FIGS. 16A and 16B are side cross-sectional and front views of a needle, respectively, suitable for advancing along the snare shaft and cutting a tract in the tissue, in accordance with an embodiment of the present invention;

FIGS. 18C and 18D are side cross-sectional views of a pull-type cutting device in a deployed or expanded configuration and a snare, in accordance with an embodiment of the present invention;

DETAILED DESCRIPTION

Figure 1:
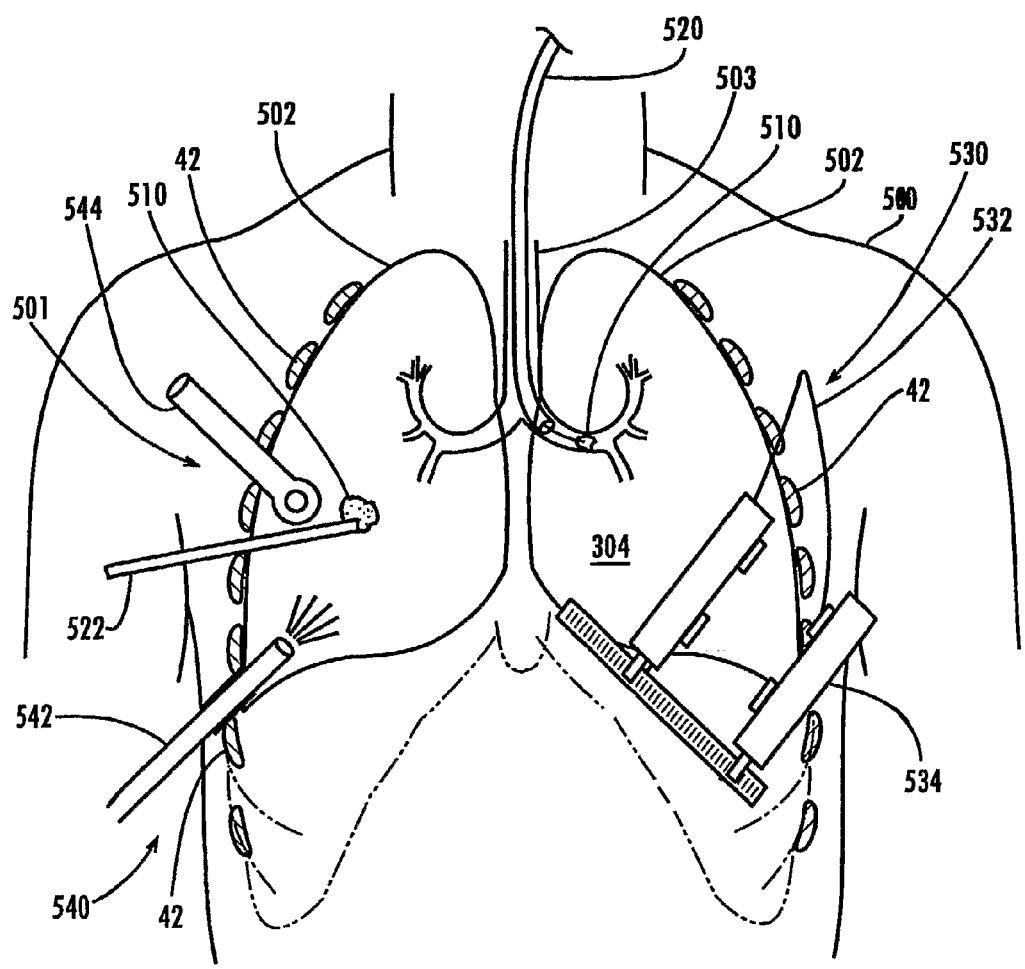
FIG. 1 is an illustration showing various prior art methods to biopsy a lung nodule.
Figure 3A:
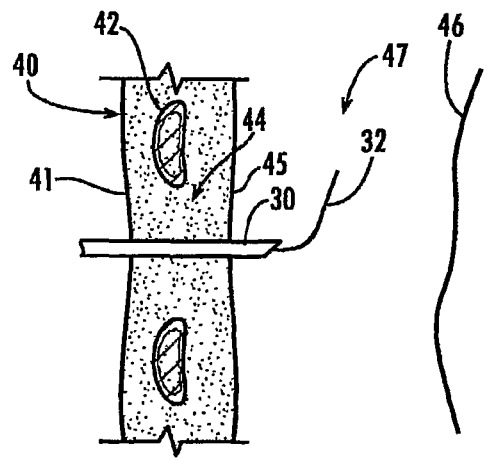
FIGS. 3A-3E are cross-sectional views showing an embodiment of a method of the present invention, wherein a body space, such as, but not limited to, a pleural space, is accessed and provided with a microport.
Figure 3B:
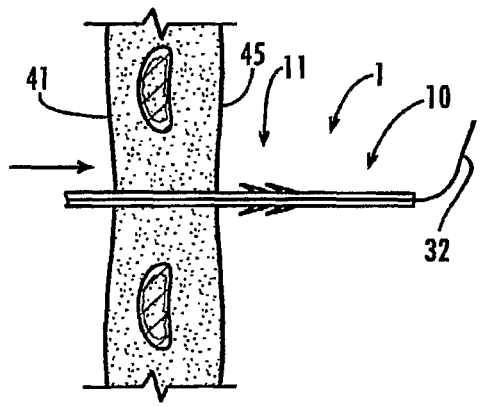
Figure 3C:
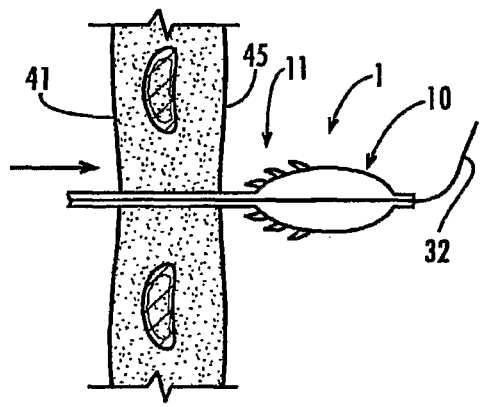
Figure 3D:
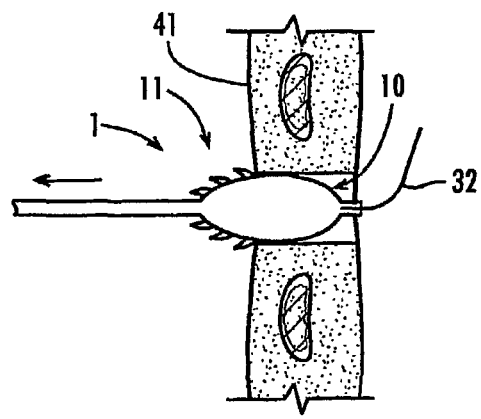
Figure 3E:
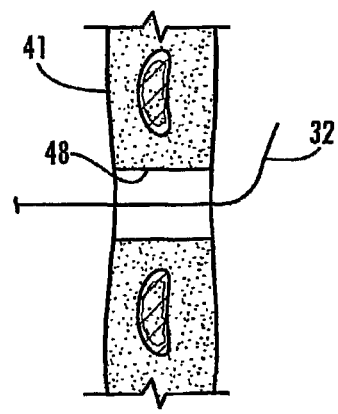

Reference will now be made to embodiments illustrated in the drawings and specific language which will be used to describe the same. It will nevertheless be understood that no limitation of the scope of the invention is thereby intended, such alterations and further modifications in the illustrated devices, as such further applications of the principles of the invention as illustrated therein as being contemplated as would normally occur to one skilled in the art to which the invention relates.

Methods and apparatus are provided to facilitate the minimally invasive removal of tissue biopsies, in accordance with embodiments of the present invention.

Methods and apparatus are provided to facilitate the direct approach to anesthetizing the chest wall, in accordance with embodiments of the present invention.

Methods and apparatus are provided to create a microport channel to introduce instruments, devices and apparatus to secure and excise lung tissue, in accordance with embodiments of the present invention.

Methods and apparatus are provided to determine if an air leak is present from a lung biopsy, in accordance with embodiments of the present invention.

Methods and apparatus are provided to drain and seal a lung tract, in accordance with embodiments of the present invention.

Methods and apparatus are provided to seal or plug a body space defect or defect in an internal lumen of the bronchus or gut, in accordance with embodiments of the present invention.

One of the challenges in performing a minimally invasive lung biopsy is how to create a small hole or port in the chest wall. In traditional thoracoscopy, when it is desired to place a thoracostomy port across the chest wall into the pleural space, or when placing a chest tube to drain fluid from the pleural space surrounding the lung, it is commonly taught that a big enough incision be made to allow the operator to finger dissect through the intercostal space, the space between adjacent ribs, into the pleural space so that any lung that is adhered to the chest wall can be dissected free prior to placing the chest tube. This will not suffice when one wishes to place 3 to 5 mm ports, as a finger dissection usually requires at least a 12 to 15 mm port. Thus, in order to make a small sized port that is far smaller than the operator's finger, currently the operator must make an incision, dissect down with a sharp instrument, and blindly push through the chest wall without feeling the underlying tissue or structures. This adds considerable risk to the procedure, as it potentially endangers the underlying critical structures such as the lung itself, the large blood vessels in the chest, the diaphragm and liver, and the heart. Thus it is commonly taught that one should never advance an instrument into the chest without manually feeling and dissecting the underlying structures to make sure they are not in proximity to the incoming sharp instrument.

Apparatus and methods are provided to create measured microports of predetermined size through body tissue, in accordance with embodiments of the present invention. The apparatus provides access to a body space through one or more small incisions, for example, but not limited to, less than 10 mm (0.4 inch), without endangering underlying structures in the space. The apparatus provides tissue cutting directed away from the critical internal structures, and towards the operator. The apparatus creates a cutting action when pulled on, and therefore, can be referred to as a pull-type cutting device.

FIGS. 2A and 2B are side cross-sectional views of a pull-type cutting device 1 in a deployed or expanded configuration and in an undeployed, deflated configuration, respectively, in accordance with an embodiment of the present invention. The pull-type cutting device 1 comprises an elongated shaft 20 having a shaft distal end 22 and a shaft proximal end 21 and a shaft lumen 23 extending there through. The pull-type cutting device 1 comprises two coaxially nested tubes, each extending from the proximal end 21 to the distal end 22; a first tube 61 and a second tube 63. The first tube 61 defines a guide wire lumen 23 extending there through adapted to slidingly receive a guide wire therein. The second tube 63 extends over the first tube 60 and coupled thereto at the shaft distal end 22. The second tube 63 defines an expandable portion 13 adjacent the shaft distal end 22. The second tube 63 defines an inflation lumen 25 extending from the shaft proximal end 21 to the expandable portion 13. The inflation lumen 25 is adapted to communicate inflation fluid from the shaft proximal end 21 to the expandable portion 13 so as to inflate and deploy the expandable portion 13 to a diameter larger than that of the deflated or pre-deployed position. Disposed adjacent the shaft distal end 22 is a cutting head 10. The cutting head 10 comprises the expandable portion 13 having a cutting portion 11 distal from the shaft distal end 22.

In an embodiment, the pull-type cutting device 1 comprises an over-the-wire balloon catheter, wherein the expandable portion 13 is a balloon, and the shaft lumen 23 is adapted to pass over a guide wire. Over-the-wire balloon catheters are known in the cardiovascular art. The cutting portion 11 is adapted to be pulled into contact with the inner wall of a body space. Extending from the cutting portion 11 are a plurality of cutting elements 12. Examples of cutting elements 12 include, but are not limited to, blades, radiofrequency, laser, and electrocautery cutting elements, that are adapted to create an incision when pulled against tissue. Since the pulling and cutting action is towards the operator, this results in an improved safety profile as it lessens the risk that an internal organ or other structure can be damaged as the body space opening is created.

In an embodiment, the device 1 is referred to as a microthoratome, adapted to make measured microports through the chest wall and adjacent or into the thoracic cavity, in accordance with embodiments of the present invention.

Other embodiments are anticipated that are directed to procedures outside of the thoracic cavity, such as, but not limited to, for accessing the peritoneal space for laparoscopy, abscess cavities, the GU tract, the air way for a tracheostomy, and blood vessels.

FIGS. 3A-3E are cross-sectional views showing an embodiment of a method of the present invention, wherein a body space 47, such as, but not limited to, a pleural space, is accessed and provided with a microport 48. Utilizing the known Seldinger technique, a needle 30 is advanced from the chest wall outer surface 41 between two ribs 42 and into the body space 47 a predetermined distance and position. A guide wire 32 is passed through the needle 30 and into the body space 47. The needle 30 is advanced and removed from the guide wire 32. The deflated pull-type cutting device 1 is advanced over the guide wire 32 by passing the lumen 23 over the guide wire 32. The cutting head 10 is placed beyond the tissue 45 to be cut. The cutting head 10 is deployed such that the cutting portion 11 is adjacent the tissue 45 to be cut. The pull-type cutting device 1 is pulled into contact with the inner surface 45 of the body space 47 such that the cutting elements 12 are pulled into contact with the inner surface 45 of the body space 47. The operator pulls the cutting head 10 towards the chest wall outer surface 41, whereby cutting a microport 48 through the tissue of the intercostal space 44 towards the chest wall outer surface 41 of the body space 47. In this fashion a microport 48 is created where the cutting direction is towards the chest wall outer surface 41 of a body space 47, rather than towards the chest wall inner surface 45. This results in an improved safety profile as it lessens the risk that an internal organ or other structure can be damaged as the microport is created.

One of the biggest areas of unmet need in thoracic surgery relates to pain control. Embodiments of the present invention are adapted to very precisely anesthetize the patient with local anesthesia prior to putting in the microports. Unlike traditional thoracotomy and thoracoscopy which is done on a patient under general anesthesia, embodiments of the present invention allow the formation of microports and subsequent procedures to be done on awake patients to minimize risks and facilitate a speedier recovery.

Apparatus and methods are provided for safe and precise access to the intercostal space for the infiltration of fluids or substances for diagnostic or therapeutic purposes, such as an anesthetic agent, in accordance with embodiments of the present invention.

Figure 4:
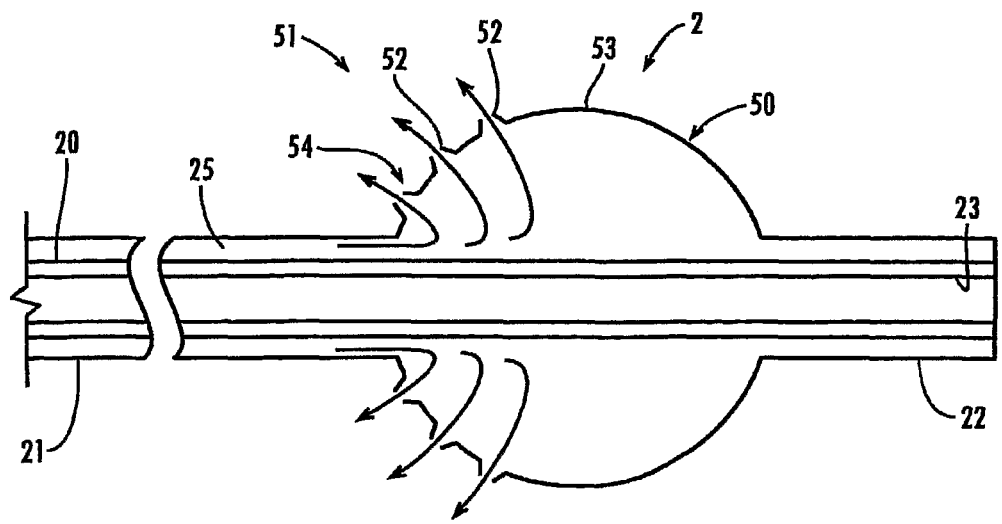
FIG. 4 is a side view of an anesthesia delivery catheter comprising a shaft having a shaft distal end and a shaft proximal end, a guide wire lumen extending there through, and a fluid lumen extending there through, in accordance with an embodiment of the present invention.
Figure 6:
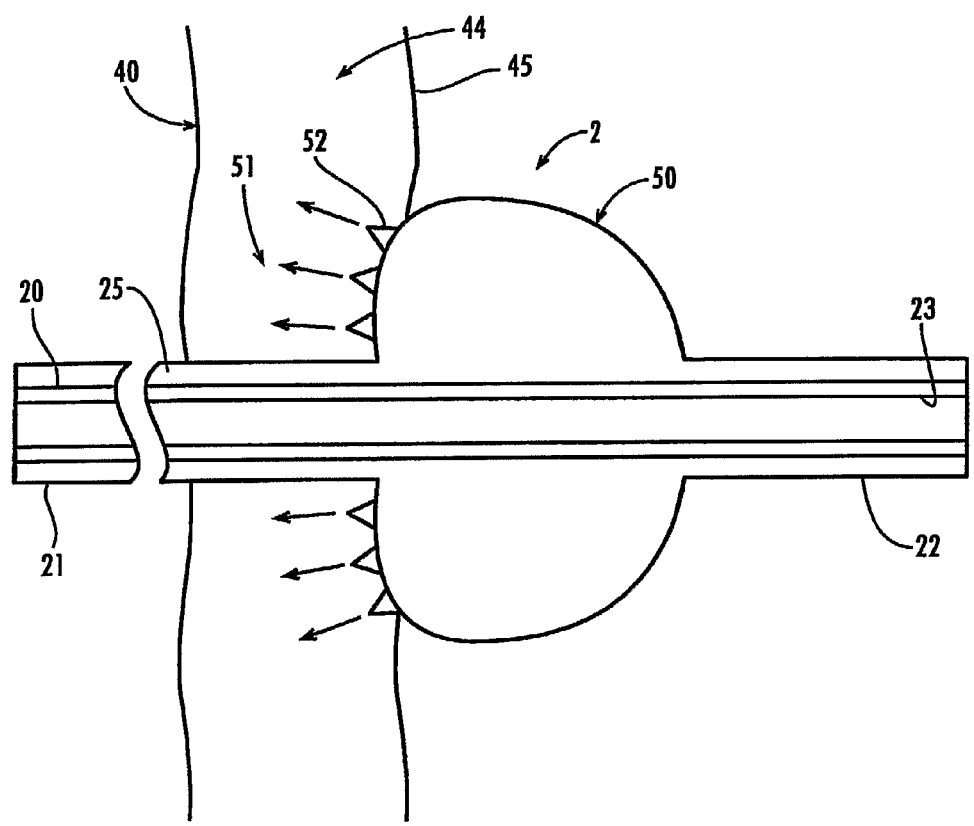
FIG. 6 is a side view of the wherein the anesthesia delivery catheter is engaged such that the delivery elements are delivering fluid to the tissue of the intercostal space, in accordance with another embodiment of the present invention.

FIG. 4 is a side view of an anesthesia delivery catheter 2 comprising a shaft 20 having a shaft distal end 22 and a shaft proximal end 21, a guide wire lumen 23 extending there through, and a fluid lumen 25 extending there through, in accordance with an embodiment of the present invention. Disposed adjacent the shaft distal end 22 is a treatment head 50. The treatment head 50 comprises an expandable portion 53 in the form of a balloon. The expandable portion 53 includes a treatment portion 51. The expandable portion 53 is in fluid communication with the fluid lumen 25 and is adapted to fill with a fluid that is introduced into a fluid lumen 25 at the shaft proximal end 21. The treatment portion 51 comprises a plurality of delivery elements 52, such as, but not limited to, hollow tines and micro introducer needles, that are adapted to extend from the treatment portion 51 and to come into contact with the pleural surface 45 of the intercostal space 44 when the expandable portion 53 is deployed, as shown in FIG. 6. FIG. 6 is a side view of the anesthesia delivery catheter 2 wherein the anesthesia delivery catheter 2 is engaged such that the delivery elements 52 are delivering fluid to the tissue of the intercostal space 44.

The delivery elements 52 comprise an aperture 54 that is in fluid communication with the fluid lumen 25. The apertures 54 are adapted to communicate a fluid from the fluid lumen 25 directly into the tissue 45 of the intercostal space 44 from "the inside out". Possible fluids for infusion into the tissue 45 include, but are not limited to, short or long acting local anesthetic agents, steroids, and neurolytic ablative agents such as alcohol or phenol.

Figure 5:
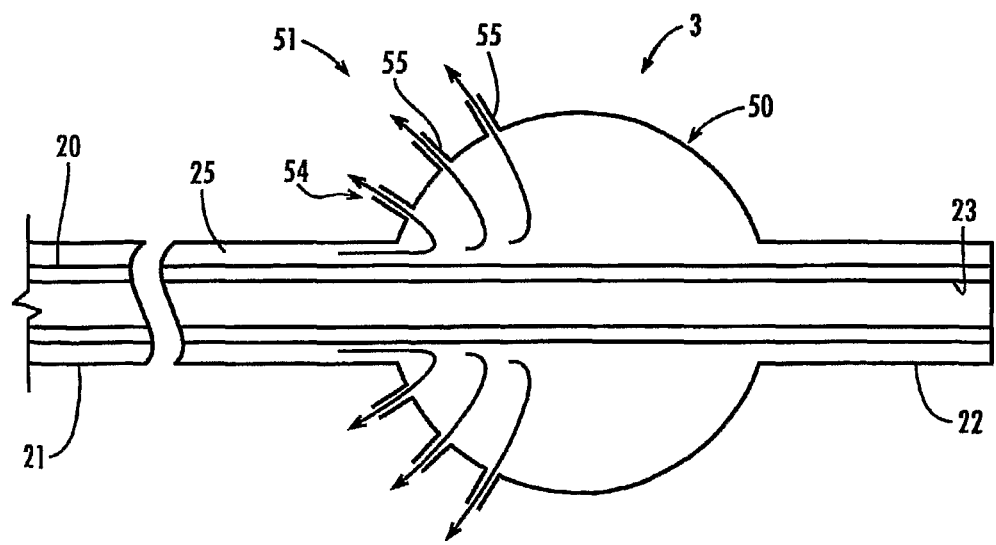
FIG. 5 is a side view of an anesthesia delivery catheter wherein the treatment head comprises delivery elements in the form of micro-needles, in accordance with another embodiment of the present invention.

Referring again to the embodiment of FIG. 4, the delivery elements 52 are in the form of a hollow cone, in accordance with an embodiment of the present invention. FIG. 5 is a side view of an anesthesia delivery catheter 3 wherein the treatment head 50 comprises delivery elements 55 in the form of micro-needles, in accordance with another embodiment of the present invention.

Figure 7A:
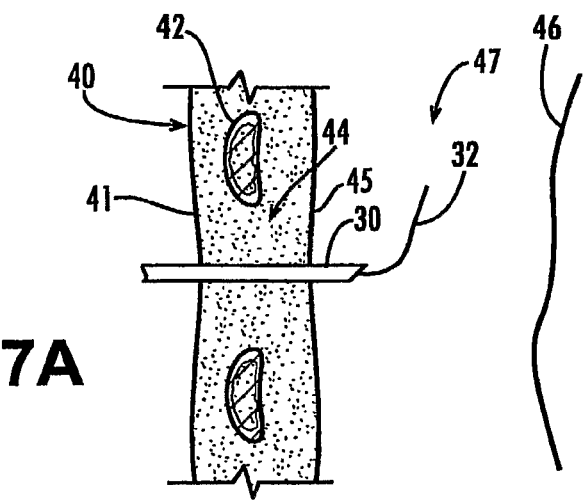
FIGS. 7A-7C are cross-sectional views showing an embodiment of a method of the present invention, wherein a body space, such as, but not limited to, a pleural space, is accessed and the intercostal space is provided with a local anesthesia, in accordance with another embodiment of the present invention.
Figure 7B:
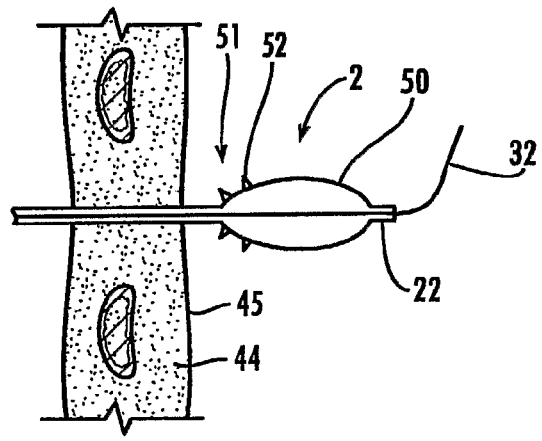
Figure 7C:
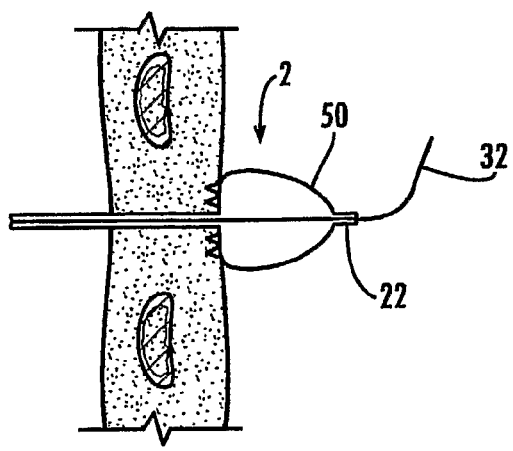

FIGS. 7A-7C are cross-sectional views showing an embodiment of a method of the present invention, wherein a body space 47, such as, but not limited to, a pleural space, is accessed and the intercostal space 44 is provided with a local anesthesia. In an embodiment of a method of the present invention, a micro-introducer needle 30 is advanced between two ribs 42 into the pleural space 47. A guide wire 32 is advanced through the needle 30 to a predetermined location beyond the needle 30. The needle 30 is removed from the guide wire 32 leaving the guide wire 32 in place. The guide wire lumen 23 of the anesthesia delivery catheter 2 is advanced over the guide wire 32 with the treatment head 50 advanced into the pleural space 47. The treatment head 50 adjacent the distal end 22 of the anesthesia delivery catheter 2 is then insufflated with a fluid, including, but not limited to, air, gas, or liquid, such as saline, water, or therapeutic substances including local anesthetic agents. The anesthesia delivery catheter 2 is then pulled back towards the operator pulling the treatment portion 51 in urging contact with the inner surface 45 of the intercostal space 44. The delivery elements 52 penetrate the inner surface 45 so as to infuse fluid into the tissue of the intercostal space 44.

This method is superior to a standard intercostal nerve block due to the precise delivery of therapeutic agent into the intercostal space. In a standard intercostal nerve block, the operator has to guess how deep to insert the needle. When it is too shallow, the nerve is missed and the therapeutic benefit is not achieved. When the needle is too deep, the therapeutic agent is instilled into the pleural space, and the therapeutic benefit is not achieved. Furthermore, if the needle is put in too deep, the lung, or other intrathoracic structures can be injured, such as the heart and great vessels, leading to a pneumothorax. While this is a risk any time a needle is inserted between the ribs into the pleural space, it is a particular concern in an intercostal nerve block when the needle is moved in and out of the space in an attempt to maximally infiltrate the space around the intercostal nerve. A needle that is too deep or too shallow is particularly a problem when infusing a neurolytic agent with the aim of ablating the nerve permanently. To minimize misplacement of the needle in the course of an intercostal nerve block, image guidance in the form of fluoroscopy is used to help guide the needle. Even with image guidance, however, it is nearly impossible to be sure that the needle is appropriately placed in a location where the treating substance can come in contact with the intercostal nerve without injuring the deeper structures, such as the lung.

In another embodiment of a method of the present invention, tumescent anesthesia is used to infiltrate intercostal tissue. Tumescent means swelling or distention. Tumescent anesthesia is commonly employed in outpatient, office-based procedures such as liposuction or endovenous saphenous vein ablation. With tumescent anesthesia, the tissues are flooded with dilute liquid anesthetic and become distended. The unique feature of tumescent anesthesia is that it involves the use of a very low concentration of local anesthetic. The large volume of fluid causes vessels to be compressed resulting in minimal bleeding. The anesthesia achieved by this technique is excellent and has a prolonged duration. This approach has allowed procedures to be employed in the out-patient setting that formerly required a general anesthetic or major regional anesthesia.

A critical component in utilizing tumescent anesthesia in a thoracic procedure is the precise infiltration of the anesthetic agent into the proper location around the intercostal nerve, without going too deep where the lung can be injured by the needle or the pleural space can be infused.

General anesthesia with single-lung ventilation is considered mandatory for any open or thoracoscopic thoracic procedure. Both thoracotomy and Video-assisted thoracoscopy surgery (VATS) are classically performed using general anesthesia, usually with a double-lumen endrotracheal tube to allow collapse of the operated lung. While thoracoscopic surgery has been performed in awake patients, the adequate delivery of anesthetic agent to the intercostal space can be challenging, even with image guidance.

Figure 8A:
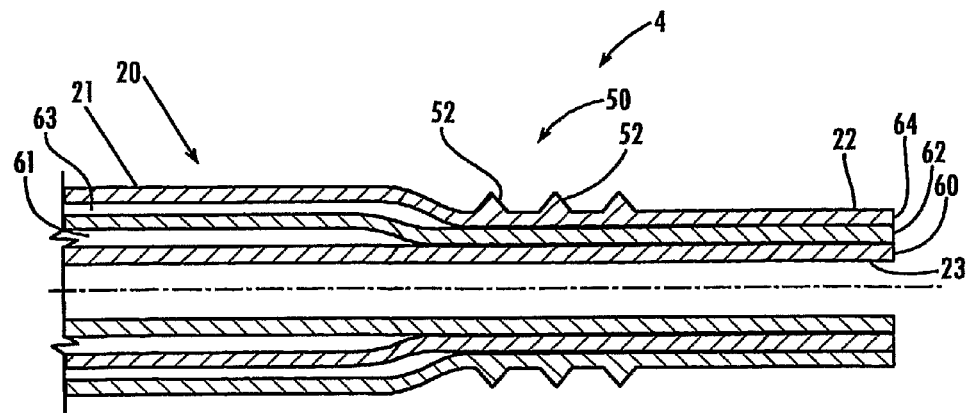
FIGS. 8A and 8B are side views of an anesthesia delivery catheter, in a pre-deployed and deployed state, respectively, comprising a shaft having a shaft distal end and a shaft proximal end, in accordance with an embodiment of the present invention.
Figure 8B:
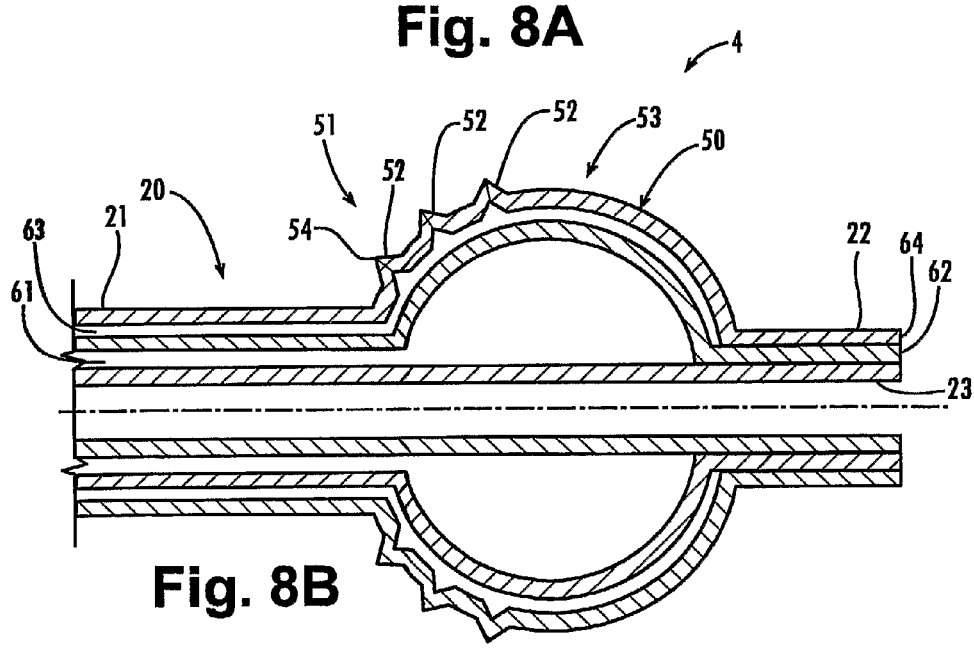

FIGS. 8A and 8B are side views of an anesthesia delivery catheter 4, in a pre-deployed and deployed state, respectively, comprising a shaft 20 having a shaft distal end 22 and a shaft proximal end 21, in accordance with an embodiment of the present invention. The delivery catheter 4 comprises three coaxially nested tubes, each extending from the proximal end 21 to the distal end 22; a first tube 60, a second tube 62, and a third tube 64. The first tube 60 defines a guide wire lumen 23 extending there through adapted to slidingly receive a guide wire therein. The second tube 62 extends over the first tube 60 and coupled thereto at the shaft distal end 22. The second tube 62 defines an expandable portion 53 adjacent the shaft distal end 22. The second tube 62 defines an inflation lumen 61 extending from the shaft proximal end 21 to the expandable portion 53. The inflation lumen 61 is adapted to communicate inflation fluid from the shaft proximal end 21 to the expandable portion 53 so as to inflate and deploy the expandable portion 53 to a diameter larger than that of the deflated or pre-deployed position.

The third tube 64 extends over the second tube 62 and coupled thereto at the shaft distal end 22. The third tube 64 defines a treatment portion 51 collocated with the expandable portion 53. The third tube 64 defines a fluid delivery lumen 63 extending from the shaft proximal end 21 to the treatment portion 51. The treatment portion 51 comprises a plurality of delivery elements 52, such as, but not limited to, hollow tines and micro introducer needles, that are adapted to extend from the treatment portion 51 and to come into contact with the pleural surface 45 of the intercostal space 44 when the expandable portion 53 is inflated. The delivery elements 52 comprise an aperture 54 that is in fluid communication with the fluid delivery lumen 63.

FIGS. 9A and 9B are side cross-sectional views of a delivery element 52, in accordance with an embodiment of the present invention. The delivery element 52 comprises extending resilient members 58 that are adapted to open under a predetermined fluid pressure to form an aperture 54 in fluid communication with the fluid delivery lumen 63 so as to allow fluid to exit the delivery element 52. The fluid delivery element 52 acts as a one-way valve to allow fluid to exit the aperture 54 but not enter.

FIG. 10 is a side cross-sectional view of a delivery element 52, in accordance with an embodiment of the present invention. The delivery element 52 comprises a micro-needle 55 having a needle lumen 57 in fluid communication with the fluid delivery lumen 63. A valve 56 between the needle lumen 57 and the fluid delivery lumen 63 is adapted to open at a predetermined pressure within the fluid delivery lumen 63, so as to allow fluid to exit the delivery element 52.

Figure 11:
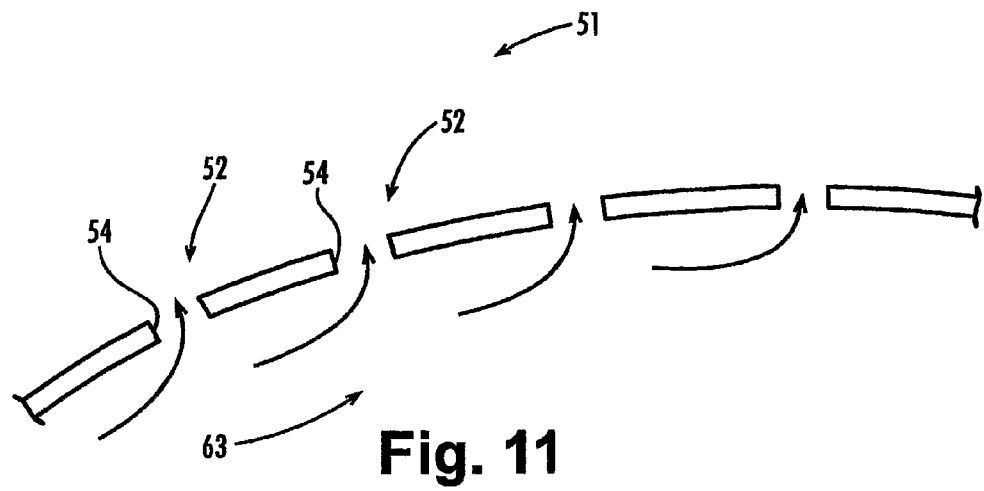
FIG. 11 is a side cross-sectional view of a delivery element, in accordance with an embodiment of the present invention.

FIG. 11 is a side cross-sectional view of a delivery element 52, in accordance with an embodiment of the present invention. The delivery element 52 comprises an aperture 54 or pore defined by the treatment portion 51. The apertures 54 are placed in urging contact with the inner surface 45 of the intercostal space 44 when the anesthesia delivery catheter 4 is pulled back towards the operator when the expandable portion 53 is inflated. Therapeutic fluid, such as anesthesia, is introduced into the fluid delivery lumen 63 at a predetermined pressure so as to expel the therapeutic fluid out of the delivery elements 52 and into the inner surface 45 under hydrostatic pressure. This type of delivery may take the form of tumescent anesthesia, used to infiltrate intercostal tissue with anesthesia fluid. Tumescent means swelling or distention. Tumescent anesthesia is commonly employed in outpatient, office-based procedures such as liposuction or endovenous saphenous vein ablation. With tumescent anesthesia, the tissues are flooded with dilute liquid anesthetic and become distended. The unique feature of tumescent anesthesia is that it involves the use of a very low concentration of local anesthetic. The large volume of fluid causes vessels to be compressed resulting in minimal bleeding. The anesthesia achieved by this technique is excellent and has a prolonged duration. This approach has allowed procedures to be employed in the out-patient setting that formerly required a general anesthetic or major regional anesthesia.

Referring again to FIGS. 7A-7C, in accordance with a method of the present invention, wherein a body space 47, such as, but not limited to, a pleural space, is accessed and the intercostal space 44 is provided with a local anesthesia. A micro-introducer needle 30 is advanced between two ribs 42 into the pleural space 47. Through the needle 30 a guide wire 32 is advanced to a predetermined location beyond the needle 30. The needle 30 is removed from the guide wire 32 leaving the guide wire 32 in place. The guide wire lumen 23 of the anesthesia delivery catheter 4 is advanced over the guide wire 32 with the treatment head 50 advanced into the pleural space 47. An inflation fluid is introduced into the inflation lumen 61 under a predetermined pressure to inflate the expandable portion 53 so as to inflate and deploy the expandable portion 53, and thus the treatment head 50. The anesthesia delivery catheter 4 is then pulled back towards the operator pulling the treatment portion 51, and thus the delivery elements 52, in urging contact with the inner surface 45 of the intercostal space 44. The delivery elements 52 penetrate the inner surface 45 so as to infuse fluid into the tissue of the intercostal space 44. Therapeutic fluid, such as anesthesia, is introduced into the fluid delivery lumen 63 at a predetermined pressure so as to expel the therapeutic fluid out of the delivery elements 53 and into the inner surface 45. Upon completion of the treatment, the introduction of therapeutic fluid is terminated and the inflation fluid is extracted from the inflation lumen 61 adapted to cause the expandable portion 53 to deflate and substantially conform to the pre-expanded state. The anesthesia delivery catheter 4 is withdrawn from the guide wire 32. The guide wire 32 is left in place.

After the intercostal space is anesthetized, a cutting catheter is advanced over the guide wire 32 and a micro-port is created substantially as provided in FIGS. 3B-3E.

In another embodiment of the present invention, this method and device is used to instill tumescent anesthesia into an awake patient for the purpose of anesthetizing an intercostal spaces. This could be used clinically for the placement of a chest tube, or the placement of intercostal ports for awake thoracoscopy. In another embodiment, the method and device is used to treat acute or sub acute rib fractures with pain or anti-inflammatory agents such as steroids. In another embodiment, the method and device is used to instill a neurolytic agent for the permanent ablation of a nerve for the purpose of chronic pain management.

Figure 8C:
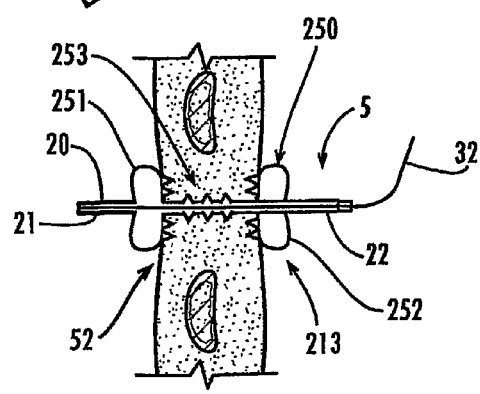
FIG. 8C is a side view of an anesthesia delivery catheter, in accordance with an embodiment of the present invention.

FIG. 8C is a side view of another embodiment of a treatment catheter 5 comprising a shaft 20 having a shaft distal end 22 and a shaft proximal end 21, a guide wire lumen extending there through, and a fluid lumen extending there through, in accordance with an embodiment of the present invention. Disposed adjacent the shaft distal end 22 is a treatment head 250. The treatment head 250 comprises an expandable portion 213 in the form of a balloon. The balloon 213 has a distal end 252 proximate the distal end 22 of the shaft 20 and a proximal end 212 distal from the distal end 22 of the shaft 20, and a balloon central portion 253 there between. The distal 252 and proximal 251 ends of the balloon 213 are larger than the balloon central portion 253; resembling a dumbbell. The balloon 213 is in fluid communication with the fluid lumen and is adapted to fill with a fluid that is introduced into a fluid lumen at the shaft proximal end. The balloon 213 has a plurality of delivery elements 52 adapted to release fluid from within the balloon 213 to external the balloon 213 at a predetermined pressure.

In another embodiment of a method of the present invention, the treatment catheter 5 is collapsed and advanced over a placed guide wire. The balloon 213 is preferentially placed within the intercostals space. The balloon 213 is pressurized with an anesthetic agent, such as, but not limited to, a tumescent anesthesia utilizing a dilute lidocaine solution. Once the intercostal space has been infiltrated with the anesthetic agent, the fluid expanding the balloon 213 is withdrawn and the balloon 213 is deflated, and the catheter 5 is removed.

In other embodiments of the present invention, the treatment catheter comprises a combination of the anesthetic instilling embodiments with delivery elements 52 with the cutting embodiments with a cutting portion 11 so that as soon as the chest wall is very precisely anesthetized, a small port can be cut by pulling the cutting element out towards the operator.

Figure 12A:
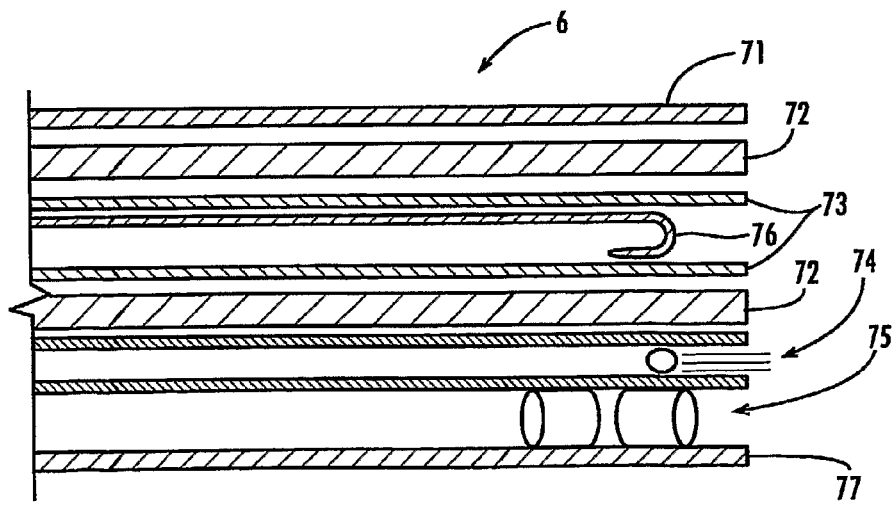
FIGS. 12A-C are side cross-sectional views of a biopsy tool for gathering a biopsy sample, such as lung tissue, in accordance with an embodiment of the present invention.
Figure 12B:
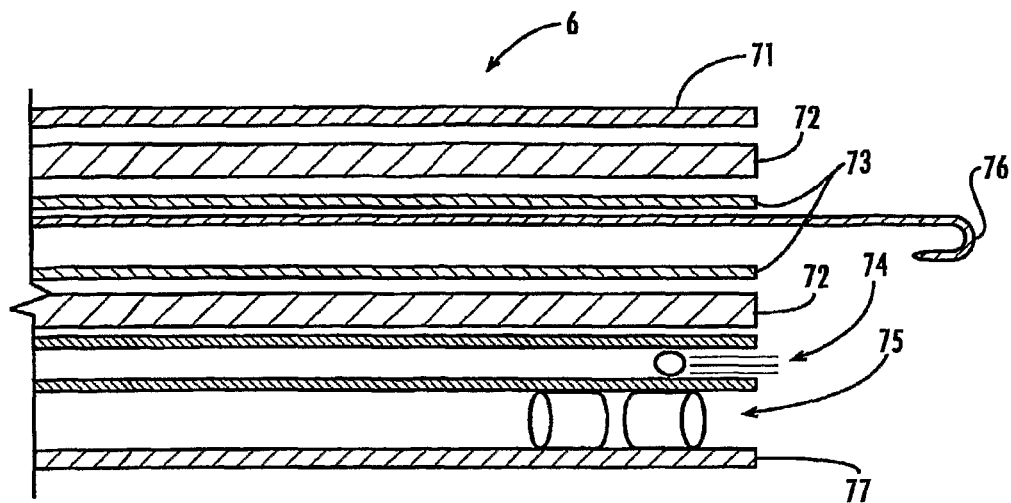
Figure 12C:
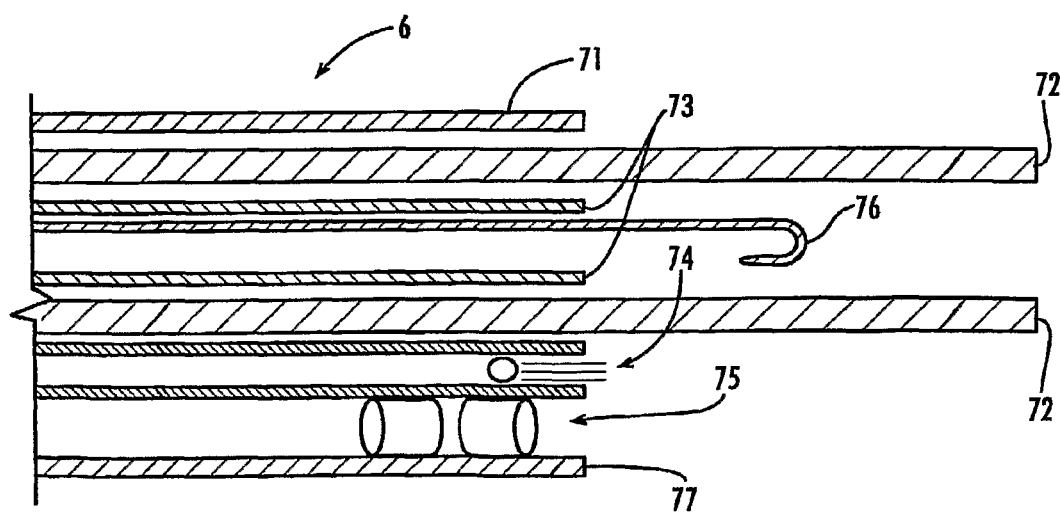

FIGS. 12A-12C are side cross-sectional views of a biopsy tool 6 for gathering a biopsy sample, such as lung tissue, in accordance with an embodiment of the present invention. The biopsy tool 6 comprises an outer sheath 71 housing a tissue cutting element 72, an endoscope 75 with light source 74, and a tissue grasping element 76. The tissue cutting element 72 and the tissue grasping element 76 are adapted to extend from and retract into the outer sheath distal end 71, suitable for a particular purpose.

FIG. 12A shows the biopsy tool 6 wherein the tissue cutting element 72 and the tissue grasping element 76 are stowed within the outer sheath 71. When stowed, the biopsy tool 6 may be inserted through a microport and into the body space, such as, but not limited to, the pleural space to adjacent the lung. FIG. 12B shows the biopsy tool 6 wherein the tissue grasping element 76 is extended from the outer sheath distal end 71 so as to couple with target tissue to be biopsied. FIG. 12C shows the biopsy tool 6 where the tissue cutting element 72 extends beyond the tissue grasping element 76 so as to sever and contain the target tissue.

In accordance with an embodiment of the present invention, the biopsy tool 6 has an outer diameter between 2 and 5 mm, suitable for insertion into microports as described above. It is anticipated that other elements may be housed within the outer sheath 71.

Figure 13A:
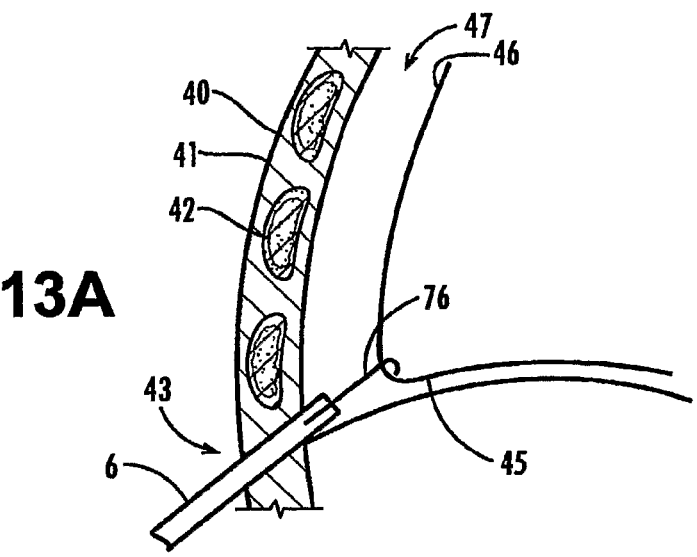
FIGS. 13A-C illustrates a method for obtaining a biopsy of lung tissue using the biopsy tool, in accordance with the present invention.
Figure 13B:
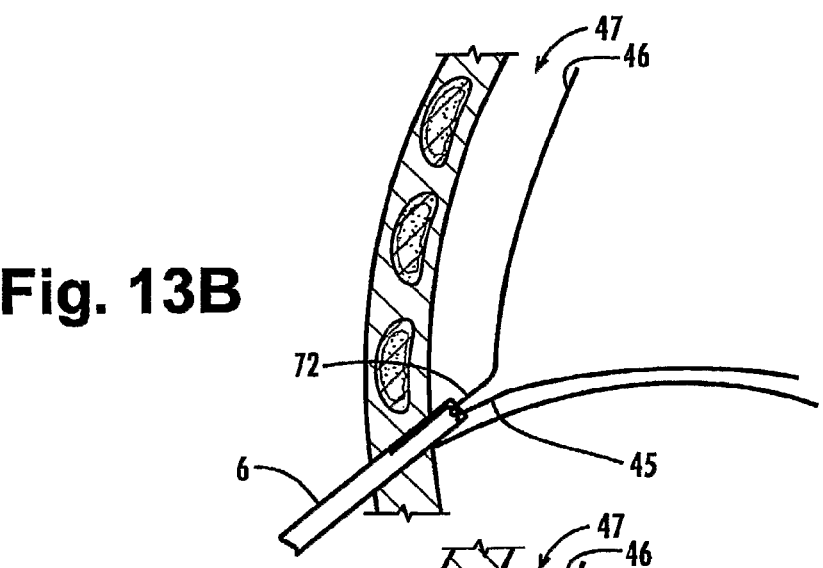
Figure 13C:
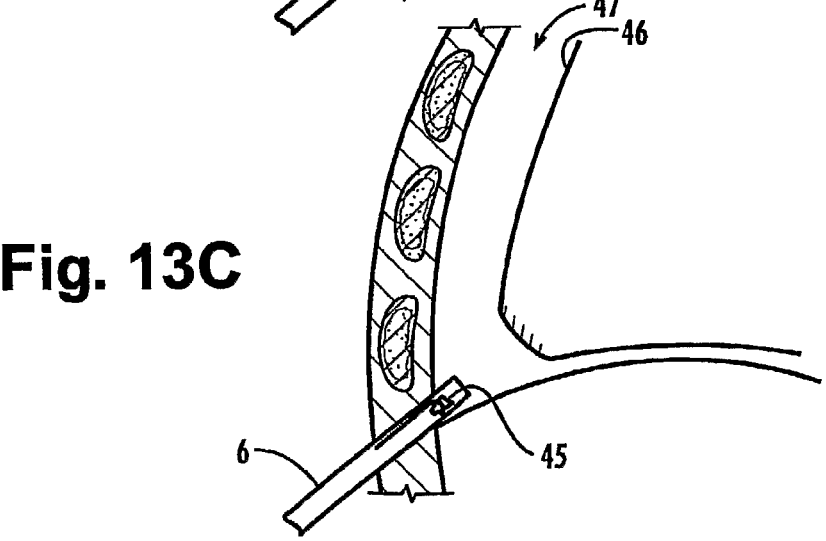

FIGS. 13A-13C illustrate a method for obtaining a biopsy of lung tissue using the biopsy tool 6, in accordance with the present invention. The chest wall 40 is anesthetized and a microport is created as provided in the embodiments above. The outer sheath distal end 77 is inserted through the microport 43 and placed in the pleural space 47 adjacent the target tissue 45 to be biopsied. The tissue grasping element 76 is extended and coupled with the tissue, as shown in FIG. 13A. The tissue grasping element 76 is retracted and/or the biopsy tool 6 is withdrawn a predetermined amount so as to stretch, elongate and thin out the tissue in preparation for severing. The tissue cutting element 72 is extended over the stretched tissue so that the target tissue is contained between the tissue cutting element 72 and the tissue grasping element 76, as shown in FIG. 13B. The tissue cutting element 72 severs the target tissue from the lung as well as seals the lung at the surgical site, as shown in FIG. 13C. The biopsy tool 6 is withdrawn from the microport with the target tissue contained within the tissue cutting element 72 and held by the tissue grasping element 76.

In an embodiment of a method for obtaining a biopsy of lung tissue using the biopsy tool 6, the method and biopsy tool 6 are adapted to sample lung tissue non-specially, as is done for a biopsy for ILD. The method to sample lung tissue utilizes a minimally invasive, direct approach where the viewing, grasping, and cutting mechanisms are all combined into one instrument that can be inserted through a small thoracoscopy. Because the approach is direct, and therefore does not require triangulation, single lung ventilation is not an absolute requirement as it is in traditional thoracoscopy. Furthermore, because the biopsy tool 6 is small, this approach can be carried out with the aid of a local anesthetic rather than a general anesthetic.

Embodiments of the endoscope 75 of the biopsy tool 6 include, but are not limited to, wherein the endoscope 75 is flexible, the endoscope 75 is rigid, wherein the endoscope 75 is fixed in the outer sheath 71, and wherein the endoscope 75 is adapted to be advanced in and out of the outer sheath 71 and fixed in a desired position to offer maximal visualization of the target tissue to be biopsied. In another embodiment, the distal end of endoscope 75 can have a variety of configurations allowing it to view from 0 degrees to 180 degrees.

It is appreciated that the tissue grasping element 76 can comprise many configurations suitable for the particular purpose. In the embodiment of FIGS. 12A-C and 13A-C, tissue grasping element 76 is a hook. In this embodiment, the hook is advanced out of the outer sheath distal end 77 towards the target tissue 45 and the tissue is "hooked" by the hooked shaped tissue grasping element 76. Once the target tissue 45 is hooked, the tissue grasping element 76 is pulled back towards the outer sheath distal end 77, stretching the target tissue 45 towards the optical system of the endoscopic 75. The tissue cutting element 72 is then used to shear off the target tissue 45 and the tissue grasping element 76 is adapted to pull the target tissue 45 into a channel where it is protected as the biopsy tool 6 is removed.

Other embodiments of apparatus and methods suitable to grasp the target tissue include, but not limited to, the use of suction to stabilize the tissue, the use of cryogenic freezing, and the use of a highly sticky polymer substance, among others.

It is appreciated that the tissue cutting element 72 can comprise many configurations suitable for the particular purpose. In embodiments of the present invention, the tissue cutting element 72 cuts the tissue while a separate element seals the surgical site. Embodiments of tissue cutting elements 72 where cutting is followed by sealing include cutting mechanisms, such as, but not limited to, a fitted scalpel blade that follows a predetermined loop beyond the extension of the tissue grasping element 76 from the outer sheath distal end 77 to cut tissue. The biopsy tool 6 further comprises a sealing element, such as, but not limited to, a stapling device, crimping device, and a compression device, such as but not limited to, an elastic band and a suture.

In other embodiments, the tissue cutting element 72 is adapted to cut the tissue and seal the surgical site. Apparatus suitable for cutting the tissue and sealing the surgical site include, but not limited to, elements incorporating radiofrequency, laser, high frequency ultrasound, and electrocautery.

When the purpose of the operation is to specifically sample a lung nodule or a very localized, specific interstitial abnormality, a thoracoscopy is of limited utility since there is no way to manually palpate the lung and localize the nodule or interstitial abnormality as is done in open surgery at thoracotomy. While some surgeons have attempted to localize tissue abnormalities with a coil or wire localized by CT, and then perform a generous wedge resection of tissue using standard lung stapling techniques, this technique is of limited utility due to the logistical challenges, as well as due to the continued need to wedge out a large area of lung so that a small nodule can be removed. Thus, an additional technical concern of the current methods of lung tissue excision is the need to create a wedge type incision in the lung to remove a nodule or interstitial abnormality. Generally the deeper the nodule in the lung parenchyma, the more lung tissue that must be removed due to the wider cut of the staples to form the wedge. As the wedge is cut, larger blood vessels and airways are cut, some of which can leak.

Leakage of air after lung stapling is a very common occurrence, and is especially common in deep wedge resections where the staple lines end up under great tension. When a lung leaks air after a lung wedge resection the patients hospital stay is considerably lengthened and their complication rate goes up significantly. Thus great attention is directed intra operatively to positioning staplers and technically managing the risk of air leak, but despite these efforts deep wedge resections can be difficult and the risk of air leak increases significantly the deeper the nodule, and the more technically challenging the wedge resection. When this occurs during thoracoscopy, the case is converted to a thoracotomy to provide the operating surgeon more access to mitigate these delicate issues.

In accordance with apparatus and methods of the present invention, there is provided a way to specifically excise lung tissue which provides a mechanism to locate a nodule or interstitial abnormality, excise the tissue and a rim of normal lung around the tissue, and seal the cutting tract. Since the number and size of the ports utilized for thoracic surgery is directly related to the amount of acute and chronic pain, desirable features include the ability to thoracscopically sample lung tissue where a single, small port, or microport, is utilized, without utilizing standard triangulation methods. In accordance with the embodiments of FIGS. 12A-C and 13A-C, methods are adapted to sample lung tissue utilizing a minimally invasive, direct approach where the viewing, grasping, and cutting mechanisms are all combined into biopsy tool 6 adapted to be inserted through a small thoracoscopy port. Because the approach is direct, and therefore does not require triangulation, single lung ventilation is not an absolute requirement as it is in traditional thoracoscopy where the lung must be deflated to allow room in the pleural space for the instruments to work. Furthermore, because the biopsy tool 6 is small, this approach can be carried out with the aid of a local anesthetic, rather than a general anesthetic.

Figure 14A:
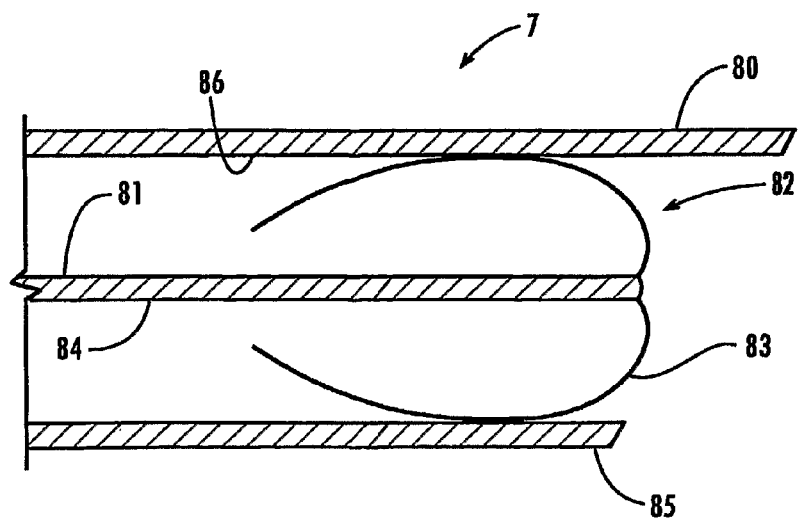
FIGS. 14A and 14B are side cross-sectional views of a biopsy tool comprising a hollow needle and a deployable and retractable snare in a retracted and deployed state, respectively, in accordance with an embodiment of the present invention.
Figure 14B:
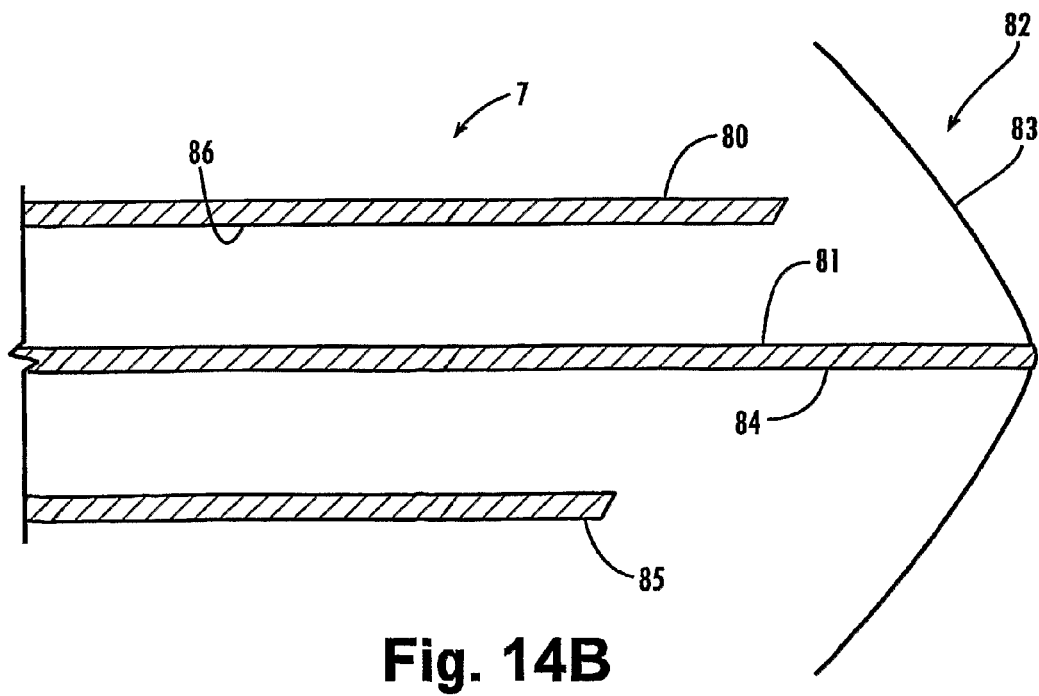

FIGS. 14A and 14B are side cross-sectional views of a biopsy tool 7 comprising a hollow needle 80 and a deployable and retractable snare 81 in a retracted and deployed state, respectively, in accordance with an embodiment of the present invention. The needle distal end 85 is sharpened so as to pass through tissue. The needle 80 defines a needle bore 86. The snare 81 comprises a snare shaft 84 and a snare head 82 at a distal end of the snare shaft 84. The snare head 82 is adapted to collapse to a low-profile state when housed within the needle bore 86, and the snare head 82 is adapted to deploy to a higher profile when extended from the needle bore 86.

The snare 81 is adapted to be advanced beyond the needle distal end 85 after the needle distal end 85 is advanced beyond the target tissue as explained below.

Figure 15A:
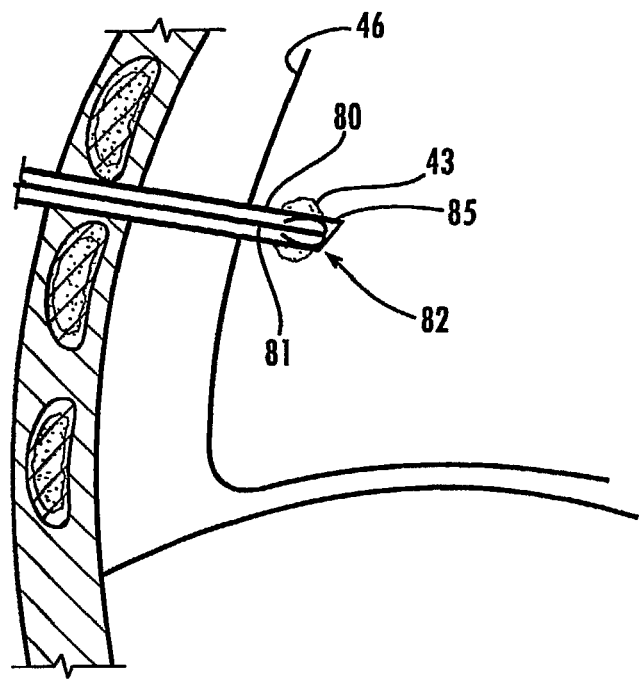
FIGS. 15A-F illustrate a method for obtaining a biopsy of lung tissue using the biopsy tool of the embodiment of FIGS. 14A and 14B, in accordance with an embodiment of the present invention.
Figure 15B:
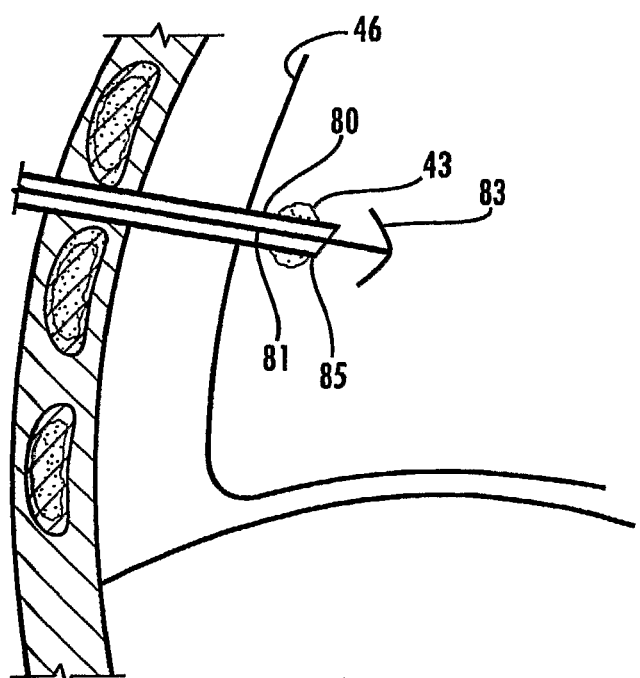
Figure 15C:
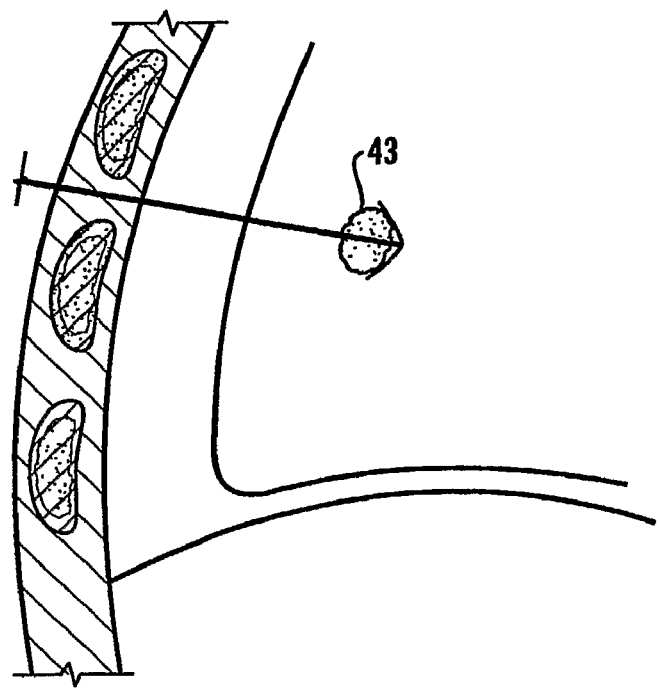
Figure 15D:
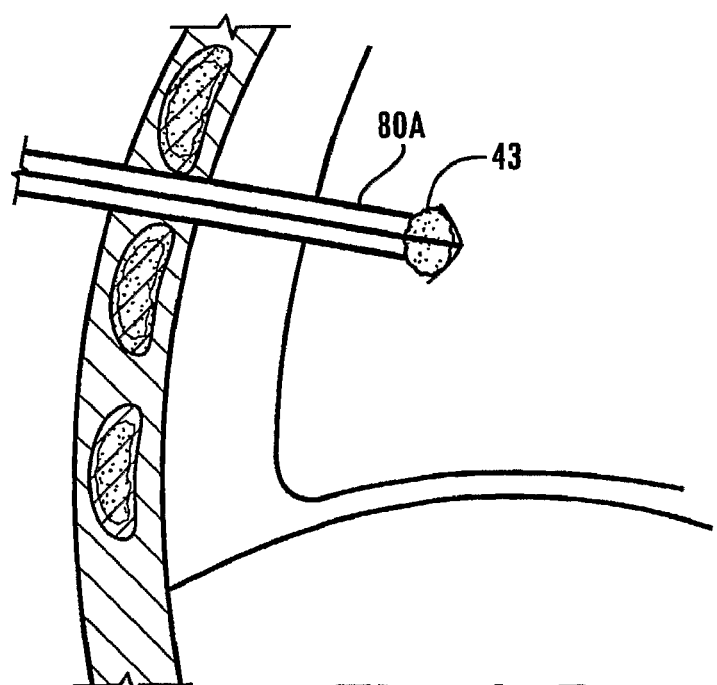
Figure 15E:
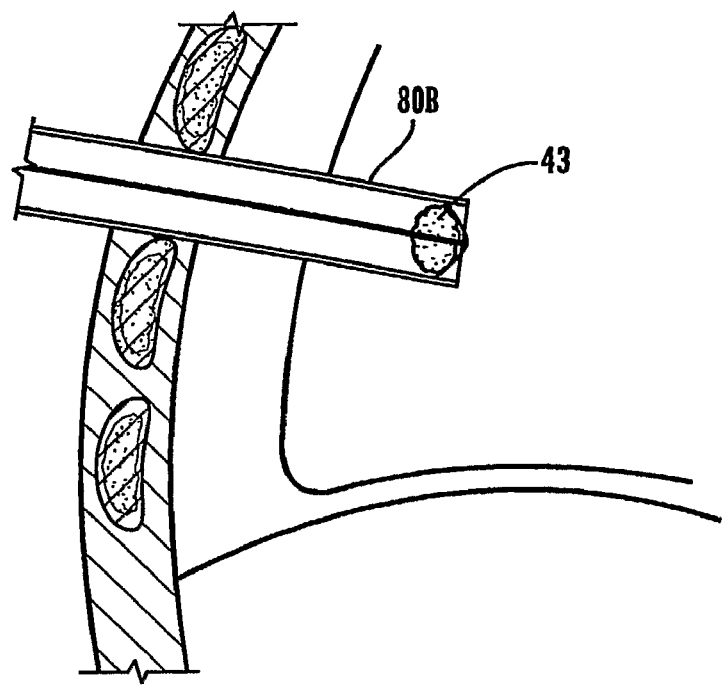
Figure 15F:
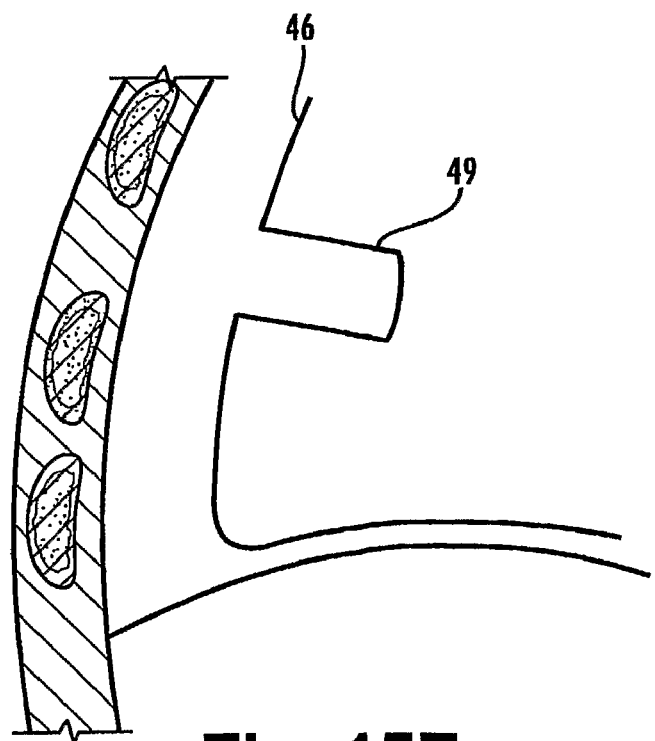

FIGS. 15A-F illustrate a method for obtaining a biopsy of lung tissue 46 using the biopsy tool 7, in accordance with the present invention. The biopsy tool 7 is advanced through the target tissue 43, a shown in FIG. 15A. The snare 81 is advanced beyond the needle distal end 85 and the snare head 82 is deployed, as shown in FIG. 15B. The target tissue 43 is therefore, between the snare head 82 and the operator. The needle 80 is slidably withdrawn along the snare shaft 84 and removed there from, leaving the snare 81 in place, as shown in FIG. 15C. One or more hollow needles 80A, 80B of increasing outer diameter, respectively, are advanced and withdrawn along the snare shaft 84 to adjacent the snare head 82 and adapted to dilate a larger tract 49 by cutting through the lung tissue 46 to the target tissue 43, as shown in FIGS. 15D and 15E. The tract having been dilated to at least the diameter of the target tissue 43, the target tissue 43 is excised and the snare 81 removed, as shown in FIG. 15F. A tract 49 cored from the lung tissue 46 can be left as is to heal or sealed to prevent bleeding and/or air leakage, as provided below.

In another embodiment of a method of the present invention, the patient has specific lung abnormality imaged. A needle 80 is passed through the chest wall and into and just beyond the lung abnormality to be biopsied, target tissue 48, such as a lung nodule. In an embodiment, the needle 80 has a tip that imparts energy to the tissue to cauterize or seal the tissue as the needle 80 is advanced. A securing or anchoring mechanism is deployed from within the needle just beyond the nodule. In one embodiment, the securing mechanism is attached to a guide wire within in the needle and running from the proximal part of the needle to the distal securing or anchoring location. From within needle, the expandable member is advanced just beyond the nodule. The expandable member comprises a cutting mechanism that when pulled backwards towards the operator, is adapted to cut a diameter of tissue that includes the nodule. In an embodiment, as the cut occurs, the tissue is sealed with an energy mechanism, such as, but not limited to, RF, Laser, HIFU, polymer sealant. The cutting member comprises a catch assembly attached to its inner diameter. The needle is removed over a wire and a series of dilating sheaths are advanced and retracted to dilate the tract up to the desired diameter. In an embodiment, each dilating sheath contains a distal tip with a mechanism to impart energy to seal the tissue as it dissects the channel. As the cutting member is pulled back towards the operator, a core of tissue that contains the nodule is excised and deposited into a catch assembly. Once the catch assembly contains the biopsy material, it is pulled in close proximity to the sheath which compresses the material to a smaller volume to aid in extraction through the tissue. Once the tract is sufficiently dilated, the catch assembly containing the biopsy material is extracted by pulling towards the operator. In another embodiment, as the catch assembly is extracted, the tissue tract is impregnated with sealant I the form of laying a core of sealant that fills the tract and prevents tissue bleeding or air leak.

FIGS. 16A and 16B are side cross-sectional and front views of needle 80A, 80B, respectively, suitable for advancing along the snare shaft 84 and cutting a tact in the tissue, in accordance with an embodiment of the present invention. The needle 80A, 80B comprises an outer tube 90 with an outer tube lumen 97, an inner tube 94 coaxial with the outer tube 90, and a plurality of blades 95 there between. The blades 95 couple with and space apart the inner tube 94 with the outer tube 90 within the outer tube lumen 97. The outer tube 90 includes an outer tube distal edge 91 that is suitable for cutting through tissue. The inner tube 94 includes an inner tube distal edge 93 that is suitable for cutting through tissue. The blade 95 includes a blade distal edge 96 that is suitable for cutting through tissue. The inner tube lumen 94 is adapted to slidingly receive the snare shaft 84 such that the needle 80A, 80B can track over the snare shaft 84 to the target tissue. Tissue cut by the outer tube distal edge 91, the inner tube distal edge 93, and the blade distal edge 96 is contained within the outer tube lumen 97 as the needle 80A, 80B is advanced through the tissue.

In an embodiment, the needle 80A, 80B comprises means for cauterizing the tissue as it is cut, such as, but not limited to, RF energy.

In an embodiment of the methods in accordance with the present invention, the tract 49 is plugged with a biodegradable material so as to seal and promote healing of the lung tissue 46. In another embodiment of the methods of the present invention, the tract 49 is compressed closed. In another embodiment, the tract 49 is sutured closed. Where drainage is required, in another embodiment, a drainage tube is placed in the tract 49 and in communication with the peritoneal space to provide for drainage.

In another embodiment in accordance with the present invention, one or more of the hollow needles of increasing diameter incorporate means for sealing the tissue. The hollow needles may incorporate means for sealing the tissue, including, but not limited to, RF, laser, cryo, among other.

In an embodiment in accordance with the present invention, methods and apparatus are adapted to sample a very specific nodule within the lung parenchyma. In accordance with an embodiment of a method of the present invention, the nodule or specific localized interstitial abnormality is localized. It is anticipated that a number of image guidance techniques can be combined with these methods to localize the abnormality.

In an embodiment of the present invention, a patient is placed in a CT scanner and the nodule is imaged. Using standard CT guided interventional techniques commonly used in CT guided biopsy of the lung, the biopsy tool 7 is advanced through the skin, chest wall, pleural space and lung and through to the target tissue 43 to be sampled. Once the distal end of the biopsy tool 7 is passed through the nodule or interstitial abnormality, a snare in the form of a compressed wire hook, such as that comprised of shape memory metal such as Nitinol, is advanced out of the distal end of the needle 80. Once the snare head 82 is advanced out of the needle, it expands to a predetermined configuration just beyond the target tissue 43.

In an embodiment, the snare head 82 has the shape of a three pronged treble hook 83. At the base of the hook 83 is the snare shaft 84, comprising, such as, but not limited to, guide wire, nylon, braided cotton string, and other flexible filaments. The needle 80 is removed, leaving the attachment filament intact in the tract to the treble hook now just beyond the target tissue 43. Once the needle 80 is removed, the operator pulls on the snare shaft 84. This engages the treble hook 83 to the target tissue, with the snare shaft 84 traversing the target tissue 43, nodule or interstitial structure, to be sampled. Once the snare shaft 84 and treble hook 83 are engaged with the target tissue 43, a sheath is passed over the snare shaft 84 and the target tissue 43 viewed with the imaging device, such as, but not limited to, CT, MRI, Ultrasound, and Fluoroscopy.

By way of example, but not limited thereto, in one embodiment the patient has a specific lung abnormality imaged. Possible techniques to image the lung include, but not limited to, CT, Ultrasound, Fluoroscopy, MRI, PET, and PET/CT. The needle 80 is passed through chest wall into and just beyond the lung abnormality to be biopsied, such as a lung nodule. In an embodiment, a needle 80 is provided comprising a tip adapted to impart energy to the tissue to cauterize or seal the tissue as it is advanced. From within the needle 80, an expandable snare 81 is extruded just beyond nodule. The expandable snare 81 is attached to a snare shaft 84, such as, but not limited to, a guide wire or guide filament, that is within the needle 80. The needle 80 is removed, leaving the snare shaft 84 coupled to the snare head 82 in place. A sheath is passed over the snare shaft 84 to dilate the track through the tissue to the distal end just before the target tissue. More than one sheath can be utilized to progressively dilate the tract. A sealing mechanism can be utilized as the tract is developed to the target tissue. Once the tract is developed to sufficient diameter, the dilating sheath is replaced with a sheath that has a distal end that can core out the target tissue or the tissue around the target tissue, and lock into the snare head 82 just beyond the area to be encompassed between the distal end of the sheath and the snare head 82. The snare head 82, now locked into the distal end of the sheath and encompassing the biopsy material, target tissue 43, the assembly is pulled back towards the operator. As the assembly is withdrawn, the surrounding tissue is cauterized. As this is done an inner channel of the guide sheath, now connected to the expandable member is utilized to deliver tissue sealant material or core plugs to fill the space and prevent air leakage.

In another embodiment of a method of the present invention, the patient has specific lung abnormality imaged. A needle 80 is passed through the chest wall and into and just beyond the lung abnormality to be biopsied, target tissue 43, such as a lung nodule. In an embodiment, the needle 80 has a tip that imparts energy to the tissue to cauterize or seal the tissue as the needle 80 is advanced. A snare head 82 is deployed from within the needle just beyond the target tissue. In an embodiment, the snare head 82 is attached to a snare shaft 84 that runs through the length of the needle 80. From within needle, the expandable member is advanced just beyond the nodule. The expandable member comprises a cutting mechanism that when pulled backwards towards the operator, is adapted to cut a diameter of tissue that includes the nodule.

In an embodiment, as the cut occurs, the tissue is sealed with an energy mechanism, such as, but not limited to, RF, Laser, HIFU, polymer sealant. The cutting member comprises a catch assembly attached to its inner diameter. The needle is removed over a wire and a series of dilating sheaths are advanced and retracted to dilate the tract up to the desired diameter. In an embodiment, each dilating sheath contains a distal tip with a mechanism to impart energy to seal the tissue as it dissects the channel. As the cutting member is pulled back towards the operator, a core of tissue that contains the nodule is excised and deposited into a catch assembly. Once the catch assembly contains the biopsy material, it is pulled in close proximity to the sheath which compresses the material to a smaller volume to aid in extraction through the tissue. Once the tract is sufficiently dilated, the catch assembly containing the biopsy material is extracted by pulling towards the operator. In another embodiment, as the catch assembly is extracted, the tissue tract is impregnated with sealant I the form of laying a core of sealant that fills the tract and prevents tissue bleeding or air leak.

Figure 17A:
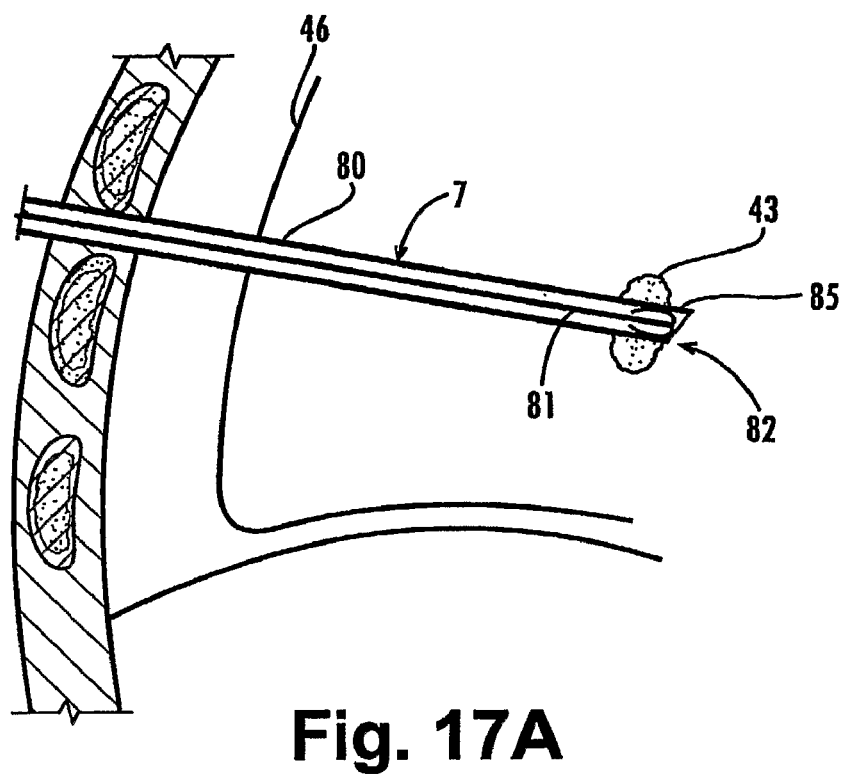
FIGS. 17A-E illustrate a method for obtaining a biopsy of lung tissue using a biopsy tool in combination with a pull-type cutting device, in accordance with an embodiment of the present invention.
Figure 17B:
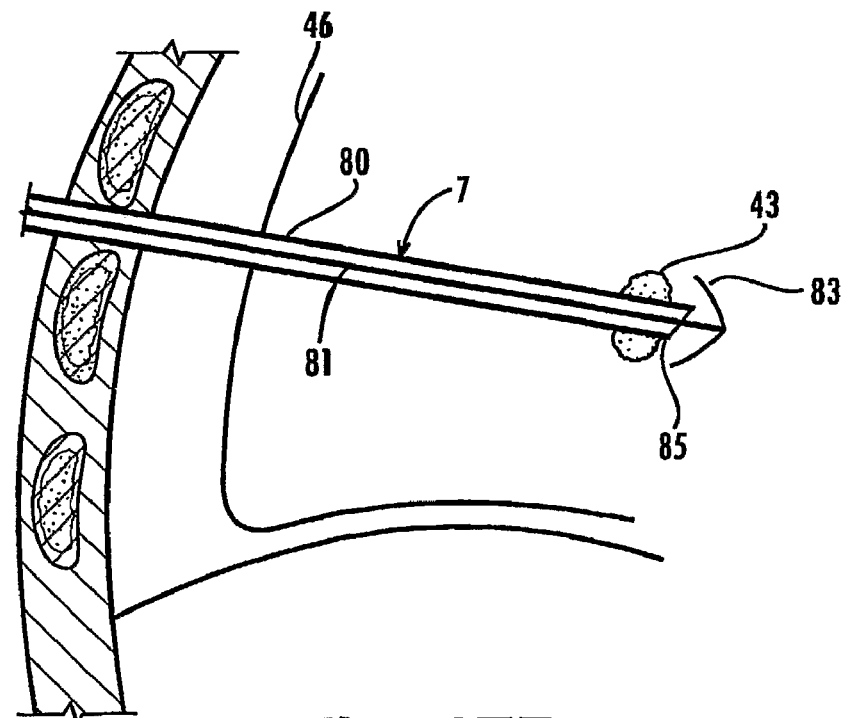
Figure 17C:
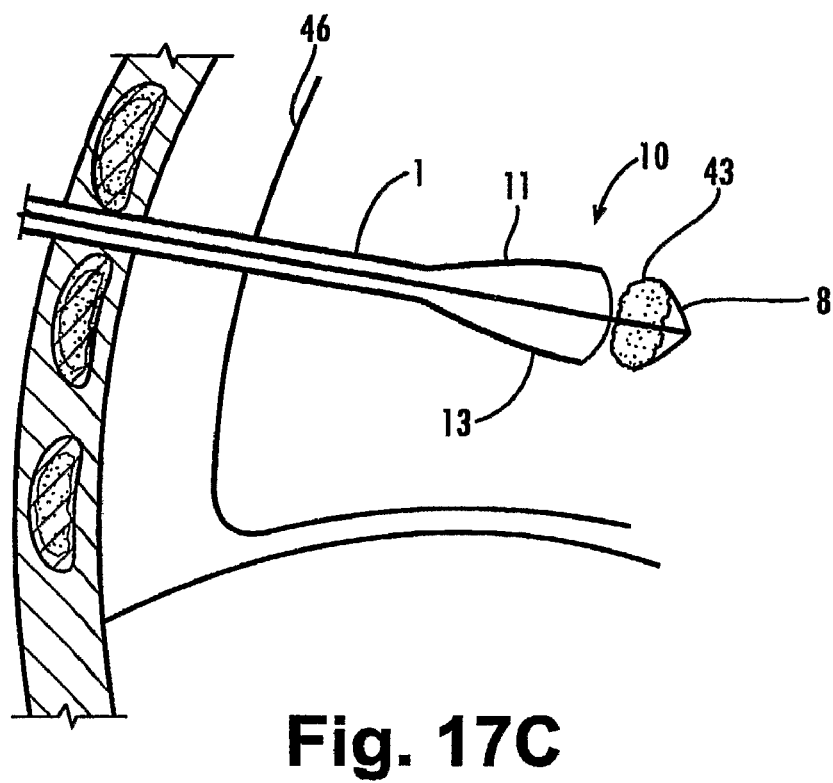
Figure 17D:
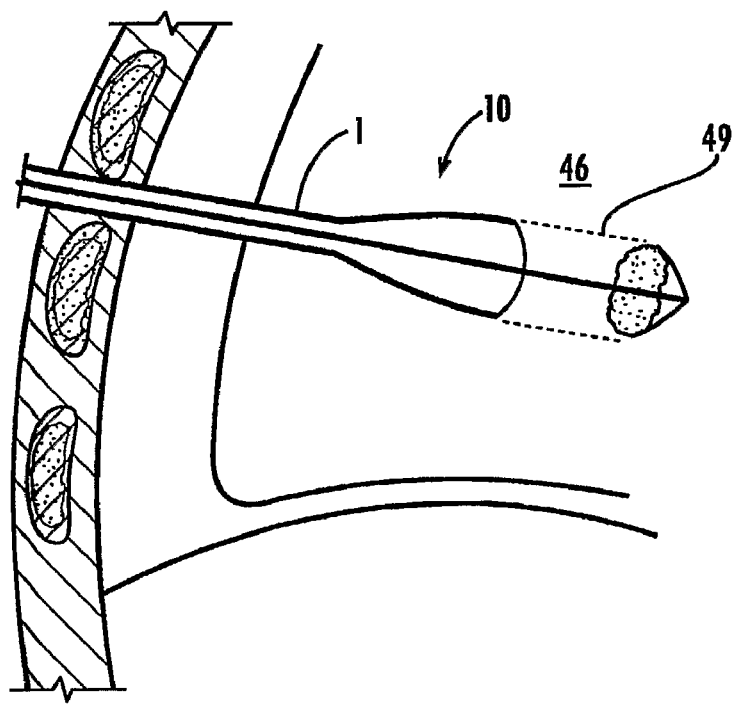
Figure 17E:
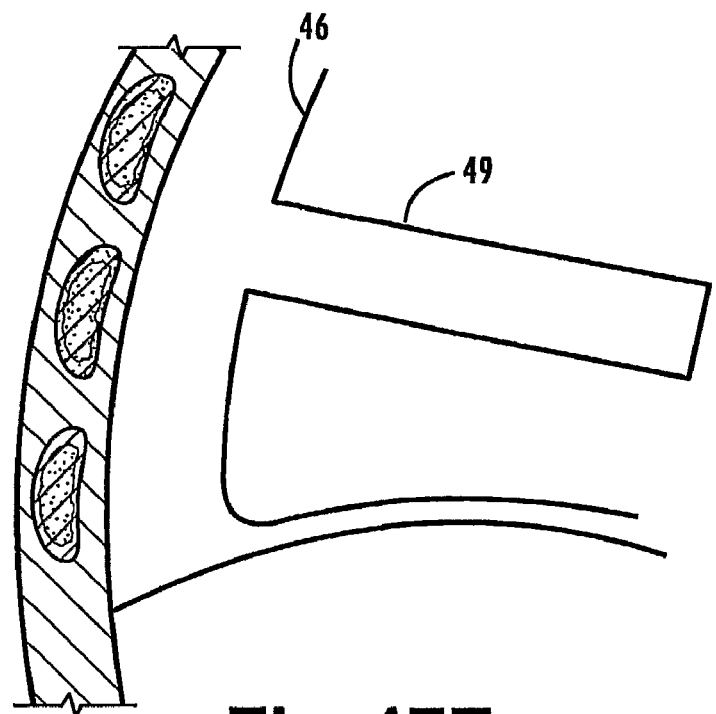

FIGS. 17A-E illustrate a method for obtaining a biopsy of lung tissue 46 using the biopsy tool 7 of the embodiment of FIGS. 14A and 14B, in combination with the pull-type cutting device 1 of the embodiment of FIG. 2, in accordance with an embodiment of the present invention. The biopsy tool 7 is advanced through to the target tissue 43, a shown in FIG. 17A. The snare 81 is advanced beyond the needle distal end 85 and the snare head 82 is deployed, as shown in FIG. 17B. The target tissue 43 is therefore, between the snare head 82 and the operator. The needle 80 is slidably withdrawn along the snare shaft 84 and removed there from, leaving the snare 81 in place. The pull-type cutting device 1 is slidably advanced along the snare shaft 84 such that the cutting head 10 is adjacent the target tissue 43. The expandable portion 13 including the cutting portion 11 is deployed, as shown in FIG. 17C. The pull-type cutting device 1 is pulled toward the operator cutting a tract 49 into the lung tissue 46, as shown in FIG. 17D. The tract 49 having been made to at least the diameter of the target tissue 43, the target tissue 43 is excised and the snare 81 removed, as shown in FIG. 17E. A tract 49 cored from the lung tissue 46 can be left as is to heal or sealed to prevent bleeding and/or air leakage, as provided below.

A variety of biopsy techniques commonly employ a small bore needles to sample tissue deep within an internal organ, or the surrounding lymph nodes for the diagnosis of cancer and other diseases. One major limitation is the amount of tissue, and thus the quantity and quality of the tissue sample for analysis. It is desirable to sample larger tissue specimens, but there are a number of difficulties in introducing large bore devices into an organ or lymph node to obtain a larger tissue sample with better preserved tissue architecture. Furthermore, while it is possible to stick a needle into most body organs with an acceptable, but not negligible complication profile, as the diameter of the access device goes up, so does the complication rate. This is especially the case in the lung, where it is desirable to sample lung nodules that are less than 1.5 cm, but the risk of bleeding and air leakage is significant. Furthermore, the proximity of major vascular structures in the lung, liver, and other locations makes the process of pushing large diameter cutting elements into the body dangerous. It is therefore also desirable to gain access deep within a solid organ or body space containing lymph nodes without endangering the tissues and vital structures around the target tissue for biopsy.

In one embodiment of the invention an instrument is provided whereby a small bore needle is advanced to a target tissue, such as a lung nodule deep in the lung, using image guidance. The needle passes through the desired tissue, and a catch and stabilization element is actuated. The nodule is secured, and cut free. With the nodule now free, the catheter traversing the specimen has the following features. The distal tip has a sealing mechanism that can include laser, RF, other energy sources, or a mechanism to deliver specific tissue sealants or plugs. Just proximal to the tissue specimen, mounted on the catheter, is an expandable cutting member that when expanded exposes a cutting element on the proximal side. The operator pulls the device back towards the outer surface of the body, along the original needle tract. As the operator pulls back, the tissue is cut, making a precisely cut channel so that the biopsy specimen, which is larger than the original needle tract, can be pulled out through the newly cut channel. As the tract is cut, the catch device enclosing the biopsy specimen is pulled out, the distal end of the catheter is utilized to seal the tract left behind.

Figure 18B:
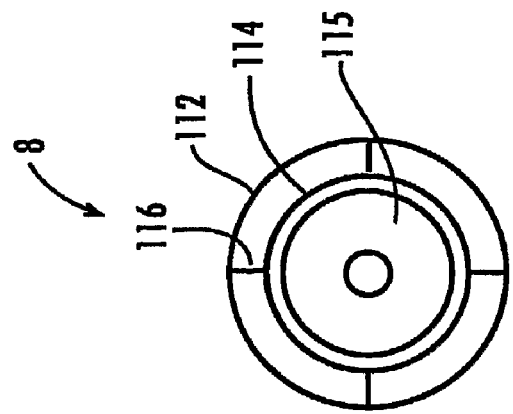
FIGS. 18A and 18B are side cross-sectional and end views, respectively, of a pull-type cutting device in a deployed or expanded configuration, in accordance with an embodiment of the present invention.
Figure 18A:
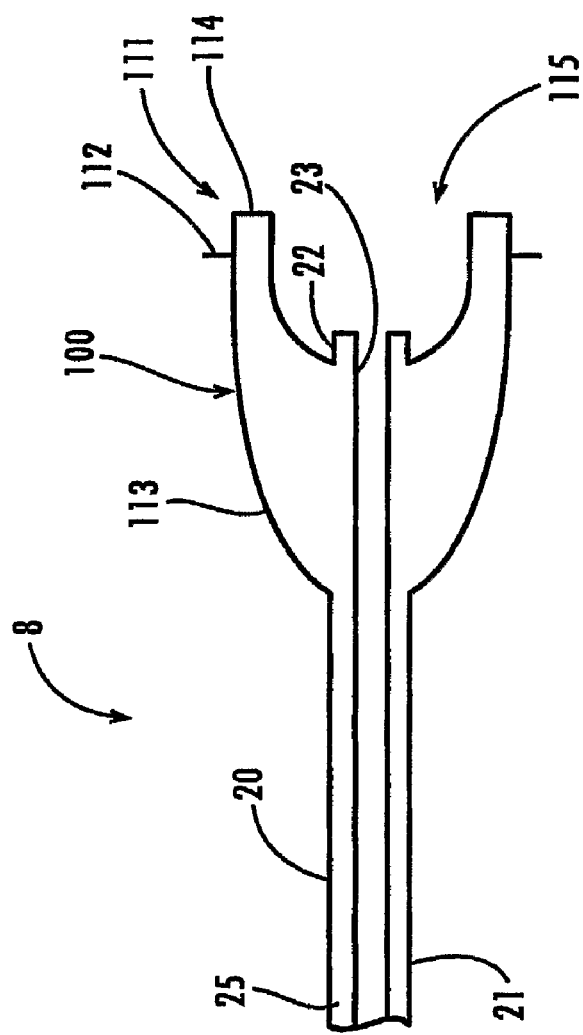

FIGS. 18A and 18B are a side cross-sectional and end view of a pull-type cutting device 8 in a deployed or expanded configuration, in accordance with an embodiment of the present invention. The pull-type cutting device 8 comprises a shaft 20 having a shaft distal end 22 and a shaft proximal end 21 and a lumen 23 extending there through. Disposed about the shaft distal end 21 is a cutting head 100. The cutting head 100 comprises an expandable portion 113 having a cutting portion 111 proximal from the shaft distal end 22. The expandable portion 113 is in fluid communication with a fluid lumen 25 which is adapted to supply fluid to the expandable portion 113 so as to inflate the expandable portion 113. The lumen 23 is adapted to pass over a guide wire or snare shaft 84. Extending from the cutting portion 111 are a plurality of stand-off blades 116 supporting a loop cutting element 112. Examples of cutting elements 112 include, but are not limited to, blades, radiofrequency, laser, and electrocautery cutting elements, that are adapted to create an incision when pulled against and through tissue. As the pull-type cutting device 8 is pulled through the tissue, the cutting element 112 cores the tissue, wherein the core of tissue can be pushed out by the subsequent pull-out of the snare 80, substantially as shown in FIG. 17D. Since the pulling and cutting action is towards the operator, this results in an improved safety profile as it lessens the risk that an internal organ or other structure can be damaged as the body space opening is created. In an embodiment, any pieces of cut tissue are deposited into cavity 115.

Figure 18C:
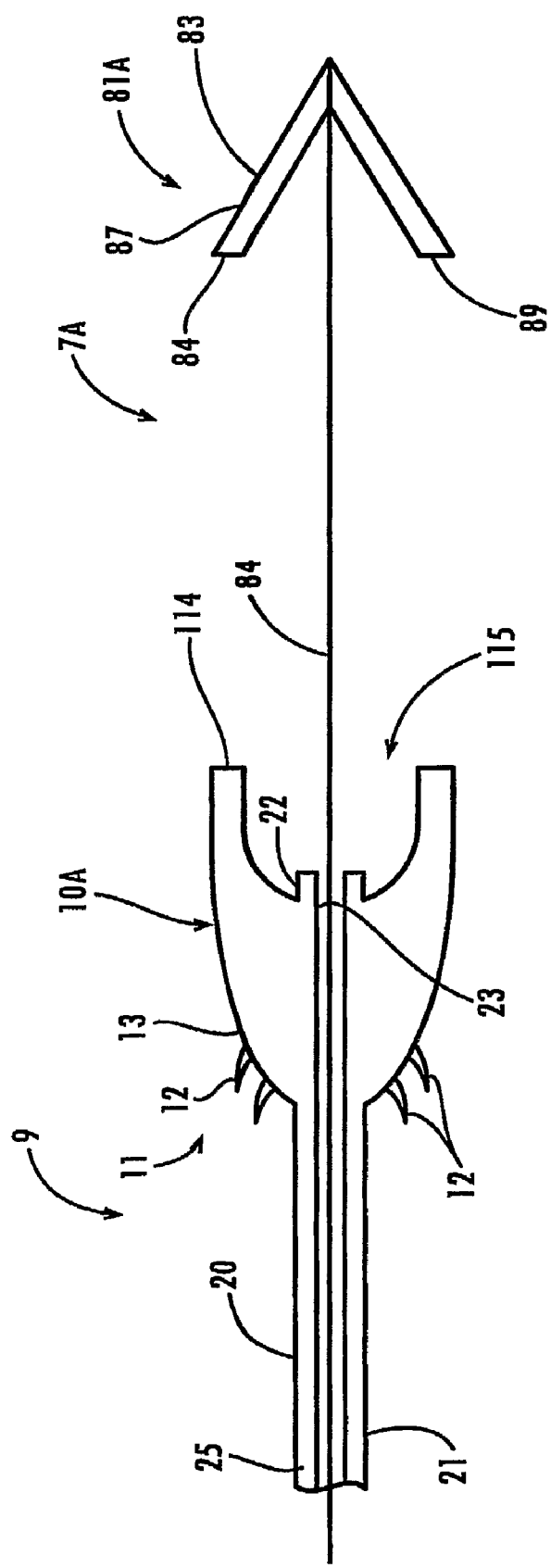

FIGS. 18C and 18D are side cross-sectional views of a pull-type cutting device 9 in a deployed or expanded configuration and a snare 81A, in accordance with an embodiment of the present invention. The pull-type cutting device 9 comprises a shaft 20 having a shaft distal end 22 and a shaft proximal end 21 and a lumen 23 extending there through. Disposed about the shaft distal end 21 is a cutting head 10A. The cutting head 10A comprises an expandable portion 13 having a cutting portion 11 proximal from the shaft distal end 22. The expandable portion 13 is in fluid communication with a fluid lumen 25 which is adapted to supply fluid to the expandable portion 13 so as to inflate the expandable portion 13. The lumen 23 is adapted to pass over a guide wire or snare shaft 84. At the shaft distal end 22, the expandable portion 13 defines a cavity 115. Extending from the cutting portion 11 are a plurality of cutting elements 12. Examples of cutting elements 12 include, but are not limited to, blades, radiofrequency, laser, and electrocautery cutting elements, that are adapted to create an incision when pulled against and through tissue. As the pull-type cutting device 9 is pulled through the tissue, the cutting elements 12 cut through the tissue. The snare 81A comprises a snare head 83 having a proximal end 89 comprising a coupling element. The expandable portion distal end 114 comprises a coupling element adapted to couple with the coupling element on the snare head proximal end 89, as shown in FIG. 18D. The snare head 83 further comprises a sealing element 87 adapted to seal the tissue as it is drawn past and through tissue.

Figure 17F:
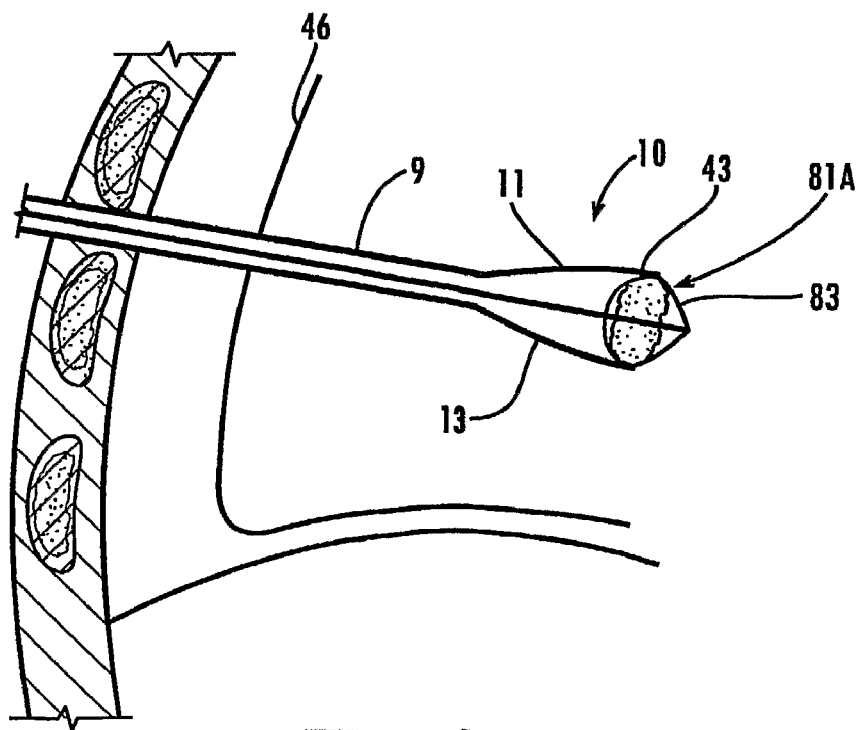
FIGS. 17F-17G illustrate a method for obtaining a biopsy of lung tissue using the biopsy tool in combination with a pull-type cutting device, in accordance with an embodiment of the present invention.
Figure 17G:
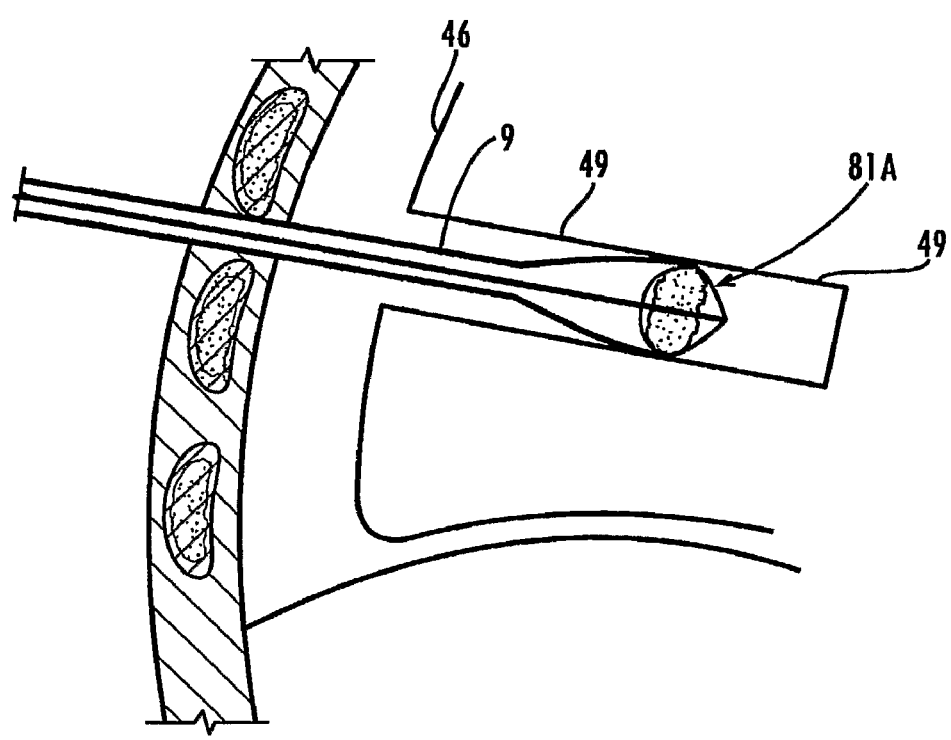

Referring again to FIGS. 17A-17B and FIGS. 17F-17G illustrate a method for obtaining a biopsy of lung tissue 46 using the biopsy tool 7,7A of the embodiment of FIGS. 14A and 14B and FIGS. 18C and 18D, in combination with the pull-type cutting device 9 of the embodiment of FIGS. 18C and 18D, in accordance with an embodiment of the present invention. The biopsy tool 7 is advanced through to the target tissue 43, as shown in FIG. 17A. The snare 81A is advanced beyond the needle distal end 85 and the snare head 82 is deployed, as shown in FIG. 17B. The target tissue 43 is therefore, between the snare head 82 and the operator. The needle 80 is slidably withdrawn along the snare shaft 84 and removed there from, leaving the snare 81A in place. The pull-type cutting device 9 is slidably advanced along the snare shaft 84 such that the cutting head 10 is adjacent the target tissue 43. The expandable portion 13 including the cutting portion 11 is deployed, as shown in FIG. 17F. The snare 81A is pulled towards the cutting head 10A with the snare head proximal end 89 placed into engagement with and coupled to the expandable portion distal end 114. The pull-type cutting device 9 and the snare 81A are pulled as a unit toward the operator cutting a tract 49 into the lung tissue 46, as shown in FIG. 17G. The tract 49 is sealed by the activation of the sealing element 87 on the snare 81A to prevent bleeding and/or air leakage.

In the following embodiments of methods in accordance with the present invention, any of the previous methods may be taken to gain image guided access to the target tissue, dilate the tract, excise the target tissue, and pull the target tissue out through the dilated tract. After the procedure, there remains a tissue tract or channel deep into the lung which potentially can bleed and leak air.

In an embodiment, a method and device is provided to drain the tract 49 while it heals from the dissection, dilation and excision from the body wall, through the pleural space to the lung parenchyma. As the lung is penetrated with the needle, and as the tract 49 is dilated and the target tissue excised, the cut surface of the lung parenchyma is prone to bleed when blood vessels are cut, and leak air when airways are cut. The method and device are adapted to provide hemostasis (no bleeding) and pneumostasis (no air leaking).

Figure 19:
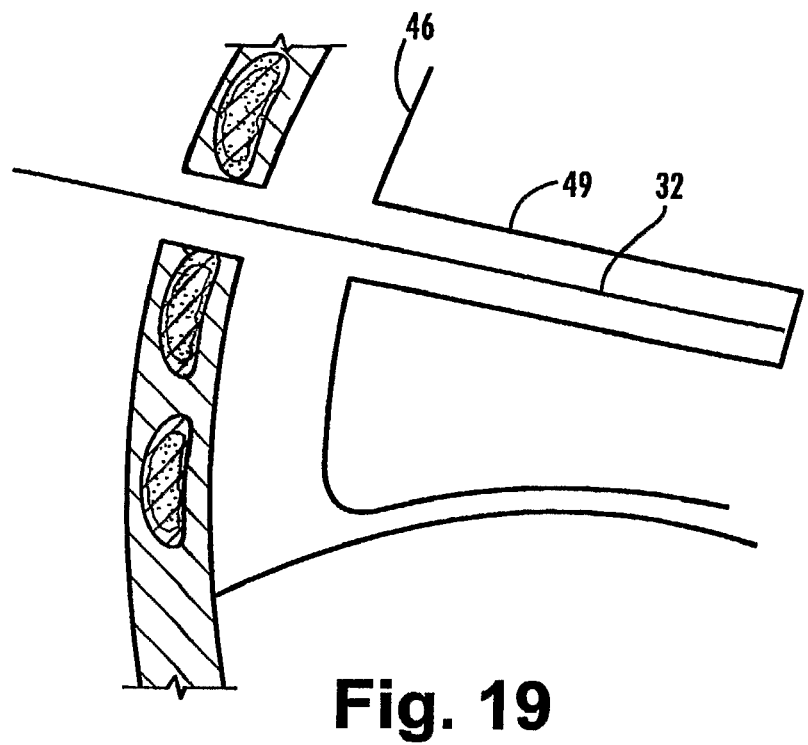
FIG. 19 is a side cross-sectional view of a tract in body tissue made in accordance with an embodiment of the present invention.

In accordance with the methods provided above, target tissue is excised resulting in a tract 49 in the tissue, as shown in FIG. 19. Upon removal of the biopsy device, a guide wire 32 is left behind in the tract 49. The guide wire 32 can be placed in the track 49 by passing the guide wire 32 through a guide wire lumen in the biopsy device, such as a guide wire lumen provided in the snare shaft 84, an accordance with an embodiment of the snare shaft 84.

Figure 20:
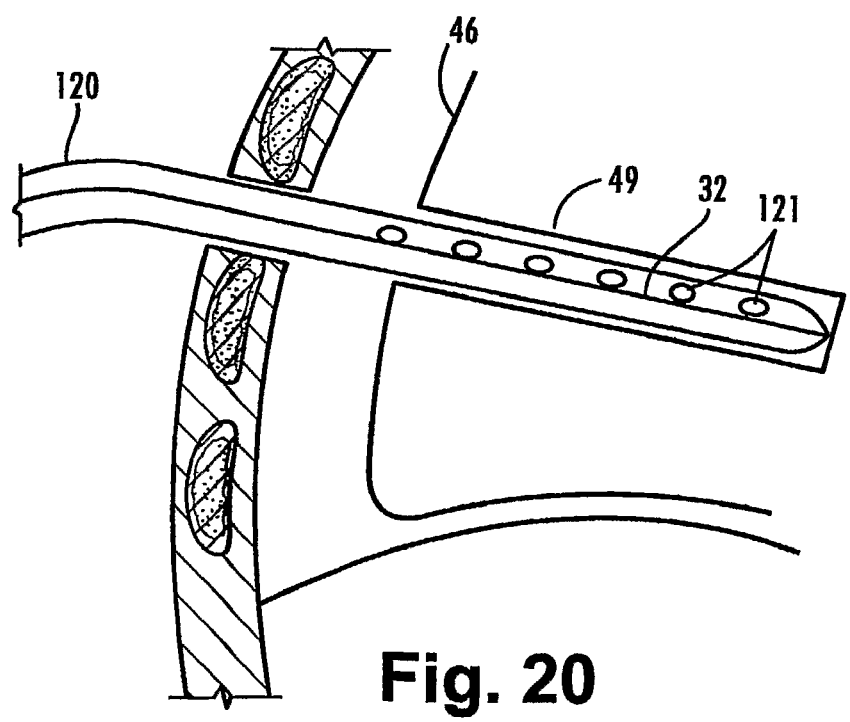
FIG. 20 is a cross-sectional view of a body space tube that has been advanced over a guide wire left in the tract after the target tissue has been extracted, in accordance with an embodiment of the present invention.

FIG. 20 is a cross-sectional view of a body space tube 120 that has been advanced over the guide wire 32 left in the tract 49 after the target tissue is extracted, in accordance with an embodiment of the present invention. The body space tube 120 comprises a plurality of apertures 121 that are positioned in the tract 49 in the lung tissue 46. The body space tube 120 is left in the tract 49 and attached to a suction apparatus to provide suction to the lung and pull the tissue in close apposition to the body space tube 120. Over a period of time, the lung tissue extraction tract 49 heals, and any blood or air is exited through the tube to an external receptacle, such as, but not limited to, a chest tube canister.

In an embodiment of the present invention, the external receptacle has a mechanism to insert a test strip into the line of air and fluid drainage, and if the test strip reacts with carbon dioxide, the color changes. If no carbon dioxide is present, the test strip does not change. The sample of gas/liquid is taken from within the pleural space to determine if air, containing carbon dioxide, is leaking out of the cut surface of the internal diameter of the tract. If it is, the tube needs to stay in place. If it is not, the tube can be removed.

This method and apparatus has applications beyond use with the lung, such as, but not limited to, cases where a chest tube is used and the question is if an air leak remains.

In an embodiment of the present invention, the body space tube 120 is biodegradable and can be cut off at the skin and left in situ.

In another embodiment of the present invention, the body space tube 120 is made of a pro-inflammatory substance that encourages inflammation and tissue in growth to limit potential for subsequent hemothorax, pneumothorax or bronchopleural fistula.

In an embodiment, the body space tube 120 is a very thin filament with multiple channels on the side. The multi channel filament left behind in the tissue tract and placed to an external suction source to drain any blood and air from the biopsy tract while the healing process takes place.

In another embodiment of the present invention, the tube with multi channels to the surrounding tract is filled with a porous sponge-like material. Suction is applied to the external lumen of the tube. The tissue around the tube is sucked down onto the tube. The porous sponge-like material keeps the lung and coagulum, fibrous material, and other material from clogging the internal diameter of the small tube while the tissue around it heals.

In another embodiment of the present invention, the body space tube 120 is drained internally to the bronchus, esophagus or peritoneal space.

Figure 21A:
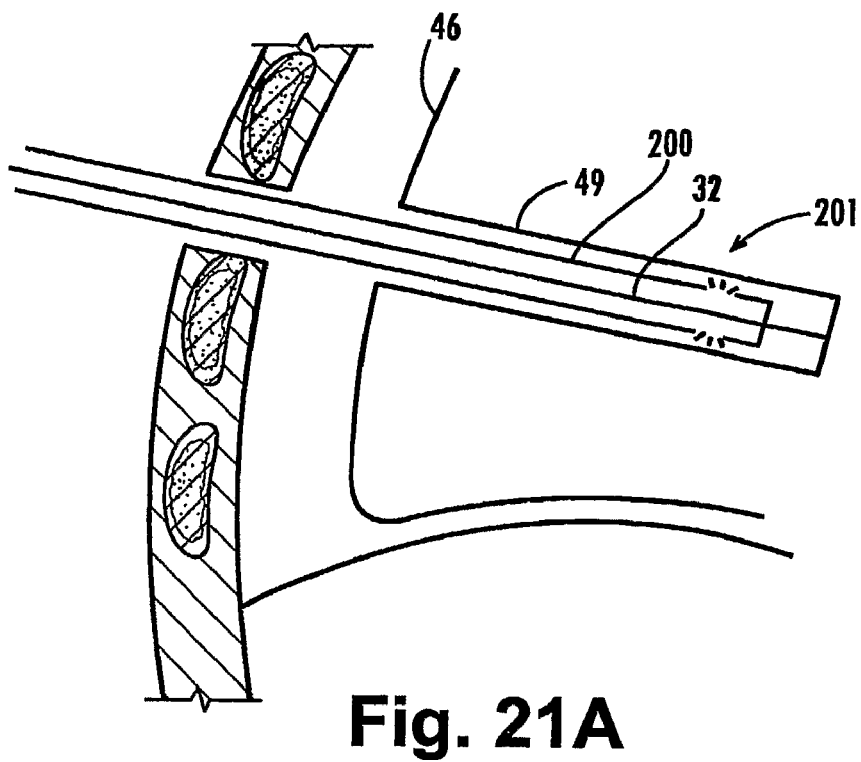
FIGS. 21A and 21B are side cross-sectional views of sealing devices, in accordance with embodiments of the present invention.

FIG. 21A is a side cross-sectional view of a sealing device 200, in accordance with the present invention. In an embodiment of the present invention, after the target tissue is extracted and a guide wire 32 is left behind in the tract 49, a sealing device 200 is passed over the guide wire 32 into the lung tissue tract 49. The sealing device 200 comprises a distal tip 201 that can impart physical energy, such as that associated with RF or Laser. Examples include, but are not limited to, diode laser, a laser of any of a number of frequencies designed to impart heat to the surrounding tissue that seals the tract. Another example provides a distal tip 201 comprising a cryogenic mechanism adapted to seal the tract 49 using cryoablation. The distal tip 201 is actuated and pulled back towards the operator. As it is pulled back the energy is imparted to the surrounding tract 49 and the tract 49 is burned and sealed, preventing the egress of blood or air.

In another embodiment, since there is no fluid in the tract 49 to be sealed, fluid is expelled through the distal tip 201 as the fluid heated with RF (i.e. Tissuelink Wet Electrode) or laser (so that the fluid becomes heated beyond the temperature of the surrounding tissue) and the tissue is sealed. The combination of the fluid and the RF seals the surrounding tissues and prevents the leakage of blood, air, lymph tissue, etc.

In another embodiment of the present invention, the sealing mechanism is contained on the outer lumen of a balloon tipped catheter. The balloon is expanded to fill the tissue tract and as the balloon is retracted towards the operator, the energy is imparted to the surrounding tissue and the tissue is sealed.

Figure 21B:
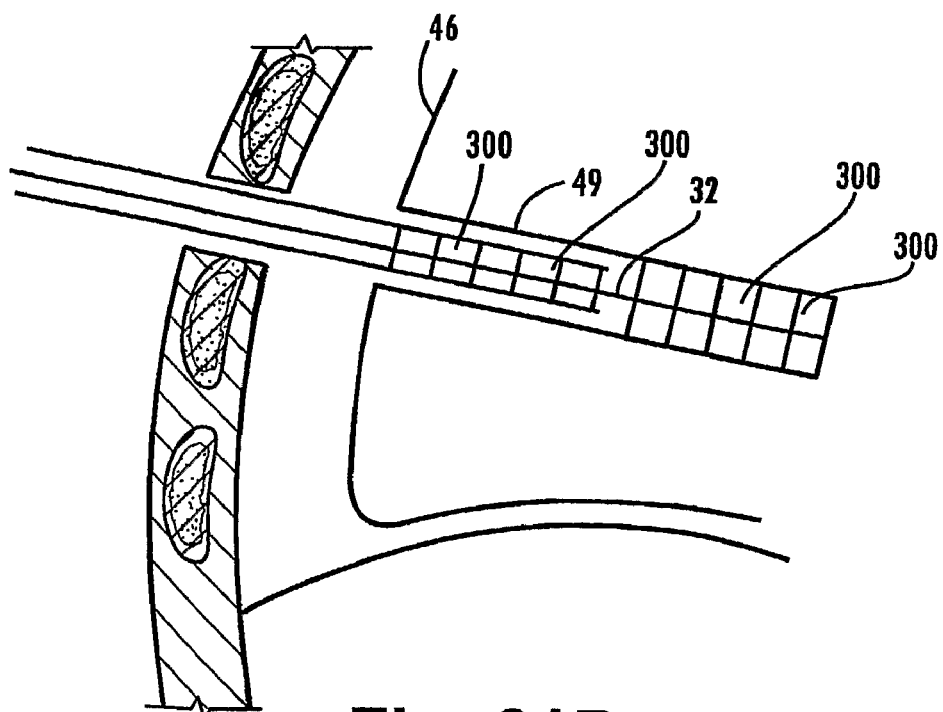

FIG. 21B is a side cross-sectional view of a sealing device 200, in accordance with the present invention including a tissue sealing substance is extruded to fill the tract 49. In an embodiment the tissue sealing substance is a polymer that increases in size or generates heat as it is actuated with an activating substance, such as external ultrasound.

In another embodiment, a spiral suture is wrapped around just under the surface of the tract 29 as it is weaved in a spiral fashion around the tract 49, and then actuated in such a fashion that the tract is pulled down upon itself and closed so there is no remaining space for blood or air to escape. In other embodiments of the present invention, other mechanisms are actuated to pull the walls of the tract down upon itself, eliminating the space for blood or air to escape.

Figure 22A:
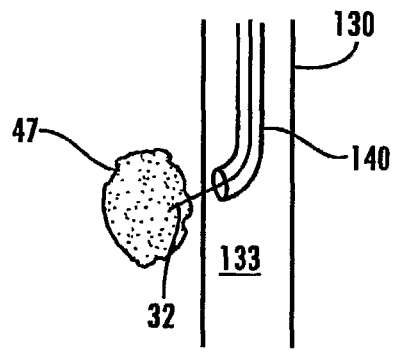
FIGS. 22A-F illustrate a method for obtaining a biopsy of target tissue that is adjacent a body lumen using embodiments of biopsy tools provided above, and a method for sealing the body lumen after the target tissue, or a portion thereof, is excised, in accordance with an embodiment of the present invention.
Figure 22D:
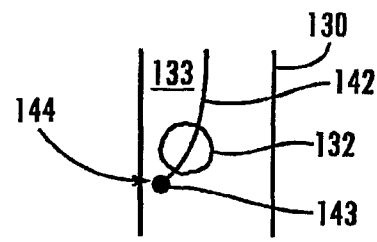
Figure 22B:
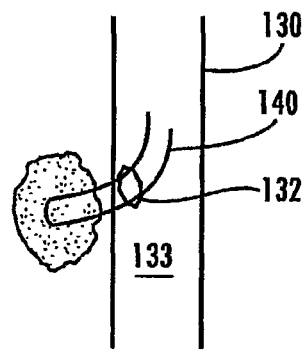
Figure 22E:
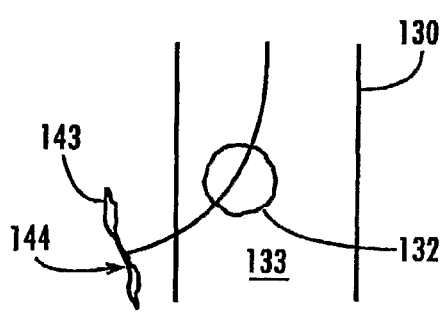
Figure 22C:
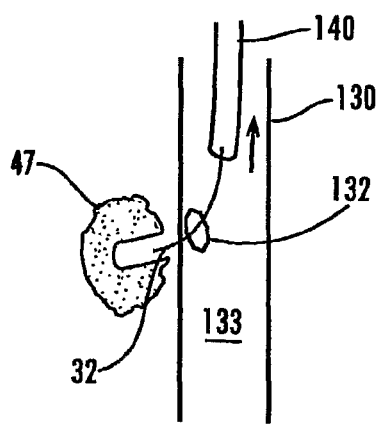
Figure 22F:
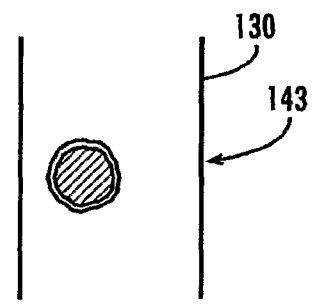

FIGS. 22A-F illustrate a method for obtaining a biopsy of target tissue 47 that is adjacent a body lumen 130, such as, but not limited to, the esophagus and bronchus, using embodiments of biopsy tools 140 provided above, and a method for sealing the body lumen 130 after the target tissue 47, or a portion thereof, is excised, in accordance with an embodiment of the present invention. Using endoscopic ultrasound or other imaging techniques, a guide wire 32 is advanced through the body lumen 130, piercing the wall 133 of the body lumen 130 and placed adjacent the target tissue 47. The biopsy tool 140 is advanced along the guide wire 32 creating an aperture 132 in the body lumen 130, as shown in FIGS. 22A and 22B. The target tissue 47 is removed using methods described above and the guide wire 32 is left behind, as shown in FIG. 22C. A sealing device 142 is provided comprising an expandable sealing element 143 at a distal end 144. The sealing device 142 is advanced over the guide wire 32 with the distal end 144 passing through the aperture 132 in the wall of the body lumen 130. The expandable sealing element 143 is expanded and pulled back against the wall 133 of the body lumen 130, covering the aperture 132.

Figure 23A:
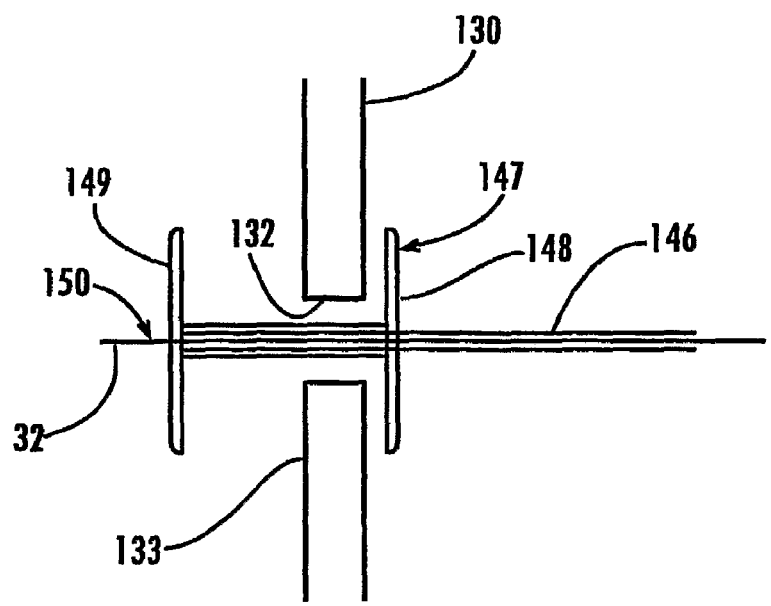
FIGS. 23A and 23B are side cross-sectional views of a sealing device adapted for sealing apertures in body lumens, in a pre-finished and finished configuration, respectively, in accordance with an embodiment of the present invention.
Figure 23B:
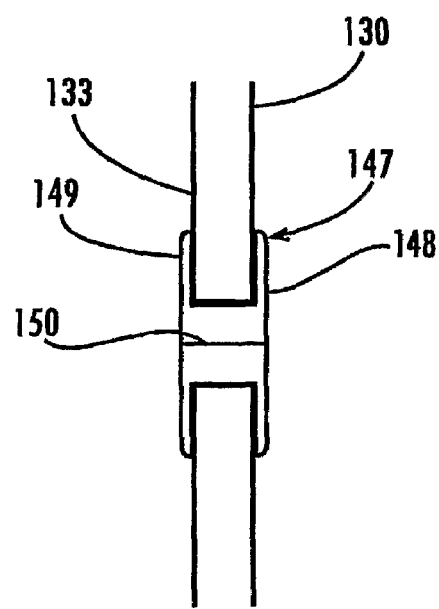

FIGS. 23A and 23B are side cross-sectional views of a sealing device 146 adapted for sealing apertures 132 in body lumens 130, in a pre-finished and finished configuration, respectively, in accordance with an embodiment of the present invention. The sealing device 146 comprises a distal end having a double-phalange plug 148. The sealing device is advanced over the guide wire 32 via a guide wire lumen 150 traversing an aperture 132 in a body lumen 130. A first phalange 149 is positioned adjacent one side of the aperture 132 and a second phalange 148 is position on the opposite side of the aperture 132. The first and second phalanges 149, 148 are brought together to impinge upon and seal the aperture 132 capturing a portion of the wall 133 adjacent the aperture 132 there between. The guide wire lumen 150 is self-sealing upon removal of the guide wire 32 there from. This embodiment can be used for esophageal perforations as well.

When a device or tube is removed from the chest, it leaves a tract from the external skin, through the chest wall to the pleural space. As the patient breaths, air can be entrained back into the pleural space, as the process breathing requires creating negative pressure within the chest relative to the external environment. When air is sucked back into the chest it creates a condition known as pneumothorax, which can be life threatening. It is generally taught to tunnel obliquely from one level to another to create a tissue flap to collapse upon itself when a tube is removed so that air cannot be sucked back into the chest. When performing thoracoscopy, however, it is desirable to tunnel directly to the pleural space, without traveling obliquely, as it facilitates the introduction and removal of the operating instruments.

In an embodiment, a method and apparatus are provided whereby a plug or series of stitches are on a wire within the chest in a compressed configuration. When it is desired to seal the pleural space, the wire is pulled back towards the operator, bringing the plug or stitches in apposition to the internal opening of the body space. The device is then actuated to insert the plug or stitches into the internal body space opening, and the wire breaks away, thereby closing the hole and preventing fluid from leaking out or air from getting sucked back in.

This embodiment could be used to seal a variety of body spaces, including surgically created internal to external port sites (such as is seen with thoracoscopy, laparoscopy), as well as to seal the bronchus, when a deep parenchymal lung biopsy is carried out from an end bronchial position. Likewise, this could be used to seal the esophagus when a transesophageal biopsy is performed, as is done for Endoscopic Ultrasound guided biopsy of mediastinal lymph nodes and other structures. This could be used for other procedures where the pleural, peritoneal or other space (GU, GYN, etc) are accessed through the gut.

One of the difficulties of CT guided biopsy of the lung is the fact that the ribs and other chest wall structures can get in the way and not provide an adequate window from which to biopsy the lung. Thoracoscopy can overcome this by starting within the pleural space, but one cannot currently localize a nodule within the lung by thoracoscopy. In this embodiment, a thoracope is fitted with an ultrasound probe on its distal tip. The tip has a lubricious covering that allows the operator to run the ultrasound probe over the surface of the lung until the nodule is localized. Once the nodule is localized, a suction apparatus around the perimeter of the ultrasound probe is actuated so that lung is sucked into the scope/probe, thus securing the area and locking the probe into place. The operator then advances a needle through the lung under ultrasound guidance to access the nodule. Then the nodulectomy can be carried out in a variety of ways, including as have been described above.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A biopsy device for use in extracting target tissue, comprising:
a first needle defining a first-needle bore, a distal end of said first needle being effective to pierce a tissue upon advancement in a patient;
a snare comprising a snare shaft and a deployable snare head at a distal end of the snare shaft, the snare shaft at least partially received within and extending through said first-needle bore, the snare head is compressed to a first, low-profile configuration while retained within the first-needle bore and deployed to a second, high-profile configuration upon advancing beyond the first-needle distal end; and a sheath insertable into said patient while accommodating said snare shaft through a bore of said sheath for guiding insertion thereof until a distal end of said sheath reaches a location adjacent said snare head, said sheath being configured to dilate a tissue tract along said snare shaft between said snare head and a space outside said patient to a sufficient diameter to accommodate withdrawal of a target tissue engaged by said snare head in said high-profile configuration, wherein the distal end of said sheath comprises a mechanism for sealing the tissue tract as the sheath is advanced into or withdrawn from the patient.

2. The biopsy device of claim 1, said sheath distal end being sharpened to core out said target tissue or a portion of tissue surrounding said target tissue for extraction thereof.

3. The biopsy device of claim 1, further comprising one or more dilating sheaths having successively increasing diameters between a diameter of said first needle and a diameter of said sheath, wherein successive ones of said dilating sheaths are insertable into and removable from said patient while accommodating said snare shaft in respective bores thereof in order to dilate the tissue tract originally created by said first needle to a larger diameter approximately that of said sheath.

4. The biopsy device of claim 3, wherein a distal end of each of the one or more dilating sheaths comprises a mechanism for sealing the tissue as the one or more dilating sheaths are advanced into or withdrawn from the patient.

5. The biopsy device of claim 3, wherein a distal end of at least one of the one or more dilating sheaths comprises a diode laser for sealing the tissue as the at least one of the one or more dilating sheaths are advanced into or withdrawn from the patient.

6. The biopsy device of claim 1, wherein the distal end of the first needle comprises a mechanism for sealing the tissue as the first needle is advanced into or withdrawn from the patient.

7. The biopsy device of claim 1, wherein the distal end of the first needle comprises a diode laser to seal the tissue as the first needle is advanced into or withdrawn from the patient.

8. The biopsy device of claim 1, wherein the mechanism for sealing the tissue tract of the distal end of said sheath comprises a diode laser to seal the tissue as the sheath is advanced into or withdrawn from the patient.

9. The biopsy device of claim 1, the snare head being made of a shape-memory material.

10. The biopsy device of claim 1, the snare head further comprising a sealing element adapted to seal the tissue as the snare head is withdrawn from the patient.

11. The biopsy device of claim 10, wherein the sealing element is an energy-imparting element adapted to cauterize tissue.

12. The biopsy device of claim 10, wherein the sealing element is an energy-imparting element adapted to produce radiofrequency energy suitable to cauterize tissue.

13. The biopsy device of claim 10, wherein the sealing element is an energy-imparting element adapted to produce laser energy suitable to cauterize tissue.

14. The biopsy device of claim 10, wherein the sealing element is adapted to extrude a polymer sealing material.

15. The biopsy device of claim 10, wherein the sealing element is adapted to expel a sealing fluid suitable to seal tissue.

16. The biopsy device of claim 15, wherein the sealing fluid is a biodegradable material suitable to form a plug.

* * * * *